(12) United States Patent
Pearl et al.

(10) Patent No.: US 7,662,113 B2
(45) Date of Patent: Feb. 16, 2010

(54) FINGERTIP TRACKER

(75) Inventors: Michael Lawrence Pearl, Los Angeles, CA (US); Joel W. Burdick, Pasadena, CA (US); Andrew Nicholas Kwok, San Jose, CA (US); Steven S. Gao, Syosset, NY (US); Kathleen E. Fischer, Dallas, TX (US)

(73) Assignee: California Institute of Technology, Pasadena, CA (US)

( * ) Notice: Subject to any disclaimer, the term of this patent is extended or adjusted under 35 U.S.C. 154(b) by 376 days.

(21) Appl. No.: 11/268,299

(22) Filed: Nov. 7, 2005

(65) Prior Publication Data

US 2006/0129070 A1 Jun. 15, 2006

Related U.S. Application Data

(60) Provisional application No. 60/625,424, filed on Nov. 5, 2004.

(51) Int. Cl.
*A61B 5/117* (2006.01)
*A61B 5/103* (2006.01)

(52) U.S. Cl. ...................... 600/587; 600/595

(58) Field of Classification Search ............ 600/587, 600/595, 407, 424, 425, 594, 427, 409; 382/103, 382/151, 152, 291; 324/226, 207.12; 702/94; 356/614

See application file for complete search history.

(56) References Cited

U.S. PATENT DOCUMENTS 3,868,565 A 2/1975 Kuipers
3,983,474 A 9/1976 Kuipers
4,017,858 A 4/1977 Kuipers
4,922,925 A 5/1990 Crandall et al.
4,988,981 A 1/1991 Zimmerman et al.
5,047,942 A 9/1991 Middleton et al.
5,316,017 A 5/1994 Edwards et al.
5,324,038 A 6/1994 Sasser
5,429,140 A 7/1995 Burdea et al.
5,444,462 A 8/1995 Wambach
5,533,531 A 7/1996 Edwards et al.
5,676,157 A 10/1997 Kramer
5,771,492 A 6/1998 Cozza (Continued)

FOREIGN PATENT DOCUMENTS

WO   WO 92/12768   6/1992

OTHER PUBLICATIONS

Flock of Birds brochure, copyright 2000.*

(Continued)

*Primary Examiner*—Max Hindenburg
*Assistant Examiner*—Brian Szmal
(74) *Attorney, Agent, or Firm*—Gates & Cooper LLP

(57) ABSTRACT

A method, apparatus, system, and article of manufacture provide the ability to utilize fingertip tracking technology during the course of a medical examination. A sensor is mounted on a fingertip of a finger of a first person. Such a sensor is communicatively coupled to a computer to record measurements. The sensor is calibrated using a known target. The finger having the sensor is then engaged to perform a medical examination directly on a second person. Measurements are obtained from the sensor on the fingertip during the medical examination. Data is obtained (e.g., via calculations or interpolation) based on the measurements.

17 Claims, 21 Drawing Sheets

U.S. PATENT DOCUMENTS

| | | | |
|---|---|---|---|
| 5,891,060 | A | 4/1999 | McGregor et al. |
| 6,049,327 | A | 4/2000 | Walker et al. |
| 6,162,190 | A | 12/2000 | Kramer |
| 6,261,247 | B1 | 7/2001 | Ishikawa et al. |
| 6,304,840 | B1 | 10/2001 | Vance et al. |
| 6,334,852 | B1 | 1/2002 | Seyl |
| 6,413,229 | B1 | 7/2002 | Kramer et al. |
| 6,491,649 | B1 | 12/2002 | Ombrellaro |
| 6,500,131 | B2 | 12/2002 | Leitner et al. |
| 6,524,260 | B2 * | 2/2003 | Shechtman et al. ......... 600/594 |
| 6,651,352 | B2 | 11/2003 | McGorry et al. |
| 2002/0198472 | A1 | 12/2002 | Kramer |
| 2005/0228270 | A1* | 10/2005 | Lloyd et al. ................. 600/424 |

OTHER PUBLICATIONS

An, K. N.; Jacobsen, M. C.; Berglund, L. J.; and Chao, E. Y.: Application of a magnetic tracking device to kinesiologic studies. *J Biomech*, 21(7): 613-20, 1988.

Burks, R. T and Schaffer, J. J.: A simplified approach to the tibial attachment of the posterior cruciate ligament, 1990.

Andriacchi, T. P.: Practical and theoretical considerations in the application in the development of clinical gait analysis. *Biomed Mater Eng*, 8(3-4): 137-43, 1998.

Andriacchi, T. P.; Dyrby, C. O.; and Johnson, T. S.: The use of functional analysis in evaluating knee kinematics. *Clin Orthop*, (410): 44-53, 2003.

Andriacchi, T. P.; Lang, P. L.; Alexander, E. J.; and Hurwitz, D. E.: Methods for evaluating the progression of osteoarthritis. *J Rehabil Res Dev*, 37(2): 163-70, 2000.

Chao, E. Y.; An, K. N.; Askew, L. J.; and Morrey, B. F.: Electrogoniometer for the measurement of human elbow joint rotation. *J Biomech Eng*, 102(4): 301-10, 1980.

Harryman, D. T., 2nd; Sidles, J. A.; Clark, J. M.; McQuade, K. J.; Gibb, T. D.; and Matsen, F. A., 3rd: Translation of the humeral head on the glenoid with passive glenohumeral motion. *J Bone Joint Surg Am*, 72(9): 1334-43, 1990.

Harryman, D. T., 2nd; Sidles, J. A.; Harris, S. L.; and Matsen, F. A., 3rd: The role of the rotator interval capsule in passive motion and stability of the shoulder. *J Bone Joint Surg Am*, 74(1): 53-66, 1992.

Harryman, D. T.; Sidles, J. A.; Harris, S. L.; Lippitt, S. B.; and Matsen, F. A., 3rd: The effect of articular conformity and the size of the humeral head component on laxity and motion after glenohumeral arthroplasty. A study in cadavera. *J Bone Joint Surg Am*, 77(4): 555-63, 1995.

Hurwitz, D. E.; Andriacchi, T. P.; Bush-Joseph, C. A.; and Bach, B. R., Jr.: Functional adaptations in patients with ACL-deficient knees. *Exerc Sport Sci Rev*, 25: 1-20, 1997.

Patriot Technical Summary, Polhemus (www.polhemus.com), Feb. 2004.

Hurwitz, D. E.; Hulet, C. H.; Andriacchi, T. P.; Rosenberg, A. G.; and Galante, J. O.: Gait compensations in patients with osteoarthritis of the hip and their relationship to pain and passive hip motion. *J Orthop Res*, 15(4): 629-35, 1997.

Hurwitz, D. E.; Sumner, D. R.; Andriacchi, T. P.; and Sugar, D. A.: Dynamic knee loads during gait predict proximal tibial bone distribution. *J Biomech*, 31(5): 423-30, 1998.

Johnson, T. S.; Andriacchi, T. P.; and Erdman, A. G.: Sensitivity of finite helical axis parameters to temporally varying realistic motion utilizing an idealized knee model. *Proc Inst Mech Eng [H]*, 218(2): 89-100, 2004.

Lai, K. A.; Kuo, K. N.; and Andriacchi, T. P.: Relationship between dynamic deformities and joint moments in children with cerebral palsy. *J Pediatr Orthop*, 8(6): 690-5, 1988.

Morrey, B. F.; Askew, L. J.; and Chao, E. Y.: A biomechanical study of normal functional elbow motion. *J Bone Joint Surg Am*, 63(6): 872-7, 1981.

Newcomer, K.; Laskowski, E. R.; Yu, B.; Larson, D. R.; and An, K. N.: Repositioning error in low back pain. Comparing trunk repositioning error in subjects with chronic low back pain and control subjects. *Spine*, 25(2): 245-50, 2000.

Pearl, M. L.; Harris, S. L.; Lippitt, S. B.; Sidles, J. A.; Harryman, D. T., 2nd; and Matsen, F. A., 3rd: A system for describing positions of the humerus relative to the thorax and its use in the presentation of several functionally important arm positions. *J Shoulder Elbow Surg*, 1: 113- 118, 1992.

Pearl, M. L.; Jackins, S.; Lippitt, S. B.; Sidles, J. A.; and Matsen, F. A., 3rd: Humeroscapular positions in a shoulder range-of-motion-examination. *J Shoulder Elbow Surg*, 1: 296-305, 1992.

Pearl, M. L.; Sidles, J. A.; Lippitt, S. B.; Harryman, D. T., 2nd; and Matsen, F. A., 3rd: Codman's paradox: Sixty years later. *J Shoulder Elbow Surg*, 1: 219-225, 1992.

Ramsey, M.; Neale, P. G.; Morrey, B. F.; O'Driscoll S, W.; and An, K. N.: Kinematics and functional characteristics of the Pritchard ERS unlinked total elbow arthroplasty. *J Shoulder Elbow Surg*, 12(4): 385-90, 2003.

Uchiyama, S.; Cooney, W. P., 3rd; Linscheid, R. L.; Niebur, G.; and An, K. N.: Kinematics of the proximal interphalangeal joint of the finger after surface replacement. *J Hand Surg [Am]*, 25(2): 305-12, 2000.

Uchiyama, S.; Cooney, W. P.; Niebur, G.; An, K. N.; and Linscheid, R. L.: Biomechanical analysis of the trapeziometacarpal joint after surface replacement arthroplasty. *J Hand Surg [Am]*, 24(3): 483-90, 1999.

Ufberg, J. and McNamara, R.: Management of common dislocations, chapter 50. 946-63, 2004.

Skeleton Builder, Motion Analysis Corporation (www.motionanalysis.com), 2004.

Flock of Birds, Ascension Technology (www.ascension-tech.com), 2004.

Flock of Birds, Real-time Motion Tracking, Ascension Technology (www.ascension-tech.com), 2000.

picBIRD, Real-time Motion Tracking, Ascension Technology (www.ascension-tech.com), 2003.

Medical & Medical Simulation, Ascension Technology (www.ascension-tech.com), 2004.

Medical FAQs, Ascension Technology (www.ascension-tech.com), 2004.

Andriacchi, T. P.; Alexander, E. J.; Toney, M. K.; Dyrby, C.; and Sum, J.: A point cluster method for in vivo motion analysis: applied to a study of knee kinematics. *J Biomech Eng*, 120(6): 743-9, 1998.

Hsu, H. C.; Luo, Z. P.; Rand, J. A.; and An, K. N.: Influence of patellar thickness on patellar tracking and patellofemoral contact characteristics after total knee arthroplasty. *J Arthroplasty*, 11(1): 69-80, 1996.

Pearl, M. L., and Wong, K.: Shoulder Kinematics and Kinesiology. Edited by Norris, T., Rosemont, AAOS, chapter 4, 2001.

Veeger, H. E.; Yu, B.; An, K. N.; and Rozendal, R. H.: Parameters for modeling the upper extremity. *J Biomech*, 30(6): 647-52, 1997.

Delp, SL, Stulberg, SD, Davies, B, Picard, F, Leitner, F.: Computer assisted knee replacement. Clin Orthop. 1998; 354:49-56.

Andriacchi, T. P.: Dynamics of pathological motion: applied to the anterior cruciate deficient knee. *J Biomech*, 23 Suppl 1: 99-105, 1990.

* cited by examiner

R - Radial
T - Tip
U - Ulnar
P - Pulp

FINGERTIP TRACKER

CROSS-REFERENCE TO RELATED APPLICATIONS

This application claims the benefit under 35 U.S.C. Section 119(e) of the following co-pending and commonly-assigned U.S. provisional patent application(s), which is/are incorporated by reference herein:

Provisional Application Ser. No. 60/625,424, filed on Nov. 5, 2004, by MICHAEL LAWRENCE PEARL, entitled "FINGERTIP TRACKER,".

This application is related to the following patents and patent applications, which are incorporated by reference herein:

U.S. Pat. No. 3,868,565, entitled "OBJECT TRACKING AND ORIENTATION DETERMINATION MEANS, SYSTEM AND PROCESS", by Jack Kuipers, filed on Jul. 30, 1973 and issued on Feb. 25, 1975;

U.S. Pat. No. 3,983,474, entitled "TRACKING AND DETERMINING ORIENTATION OF OBJECT USING COORDINATE TRANSFORMATION MEANS, SYSTEM AND PROCESS", by Jack Kuipers, filed on Feb. 21, 1975 and issued on Sep. 28, 1976;

U.S. Pat. No. 4,017,858, entitled "APPARATUS FOR GENERATING A NUTATING ELECTROMAGNETIC FIELD", by Jack Kuipers, filed on Feb. 24, 1975 and issued on Apr. 12, 1977;

U.S. Pat. No. 4,988,981, entitled "COMPUTER DATA ENTRY AND MANIPULATION APPARATUS AND METHOD", by Thomas G. Zimmerman and Jaron Z. Lanier, filed on Feb. 28, 1989 and issued on Jan. 29, 1991; and U.S. Patent Application Publication No. 2002/0198472 (application Ser. No. 09/730,056), entitled "DETERMINATION OF FINGER POSITION", by James F. Kramer, filed on Dec. 5, 2000, which application is a continuation of application Ser. No. 08/947,491, filed on Oct. 10, 1997, now U.S. Pat. No. 6,162,190, which is a continuation of application Ser. No. 08/172,868, filed on Nov. 26, 1993, now U.S. Pat. No. 5,676,157, which is a continuation of application Ser. No. 07/909,570, filed on Jul. 6, 1992, now abandoned.

BACKGROUND OF THE INVENTION

1. Field of the Invention

The present invention relates generally to tracking fingertip movement, and in particular, to a method, apparatus, and article of manufacture for precisely tracking the location of fingertips during a medical examination. More specifically, the location is tracked while the fingertips palpate physical structures or manipulate appendages during medical exams or therapies.

2. Description of the Related Art (Note: This application references a number of different publications as indicated throughout the specification by reference numbers enclosed in brackets, e.g., [x]. A list of these different publications ordered according to these reference numbers can be found below in the section entitled "References." Each of these publications is incorporated by reference herein.)

During the course of medical examinations, therapies, or surgeries, medical doctors in a very wide variety of medical specialties palpate physical structures or manipulate joints, bones, or appendages. For example, recognizable points of a human skeleton may be palpated, range-of-motion measurements may be conducted, and fractured bones may be reduced using a physician's fingers. Further, many areas of medicine require a physician or medical specialist to measure the size and depth of physical structures for the purposes of diagnosis of injury or disease, planning therapeutic interventions, or monitoring the patient recovery process. Despite the fact that such measures are made and recorded literally millions of time per day, it is current practice for physicians to estimate or guesstimate the size of critical dimensions based on fingertip placements. Such measurements are often only accurate to 30%. Nonetheless, such measurements are routinely used for diagnosis, treatment planning, assessing treatment outcomes, and as the basis for clinical trials that assess the validity of new treatments. Moreover, such data is often the basis for disability insurance reimbursements legal remuneration for injury.

These problems may be better understood with an explanation of prior art medical examination techniques and computer-assisted tracking methodologies.

Medical Examination Techniques

In the practice of orthopedics, the ability to palpate recognizable points of the human skeleton is an essential skill for diagnosis and treatment. Skeletal bones have consistent protrusions that aid the examiner in localizing the bone in order to frame the rest of the examination. For example, the medial and lateral epincondyles of the knee, along with the perimeter of the patella and the tibial tubercle create a framework from which the examiner can palpate adjacent ligamentous structures such as the medial collateral ligament and the knee menisci. FIG. 1 illustrates the prominent bony landmarks around the knee and up to the hip. Similarly, the medial and lateral epincondyles of the elbow, and radial and ulnar styloids of the forearm are prominent points that define the distal humerus and forearm. FIG. 2 illustrates the prominent bony landmarks around the elbow. In the shoulder as illustrated in FIG. 3, the posterior corner of the acromion, the coracoid, the inferior angle and the scapular spine can easily be accessed to generate a representation of this bone.

The cluster of points that represent a given bone are informative in their own right but can also form a foundation that can be used in a variety of ways. For example, accurate representation of the skeleton provides the basis for defining the relative motion between any adjacent skeletal segments. If the two segments are connected, the range of motion so measured defines the range of motion of the interposed joint. Thus, on its own, skeletal information provides a three dimensional representation of size and proportion of each skeletal segment. Taken together, data of multiple bones begins to define the size and proportion characteristics that distinguish one individual from another. Precise information of these individual differences has great application to many fields and is largely inaccessible in other ways with the exception of radiography. This information has import not only to clinical medicine, but also to fields as disparate as clothes manufacturing and game development using motion capture technology.

As described above, measuring joint range-of-motion is an integral part of clinical orthopedics. Range of motion measurements are a standard part of nearly every orthopedic exam. FIG. 4 illustrates skeletal landmarks used to construct a local coordinate system to define the range of motion with precision. In FIG. 4A, planes of elevation for a scapular based coordinate system are shown from a superior view. In FIG. 4B, the angle of elevation is shown with respect to a scapular reference. FIG. 4C illustrates a global diagram based on a scapular coordinate system showing rotation (45°) referenced to the latitude. Typically, the examiner moves a joint through its range of motion and makes a visual estimate of the angular changes observed. For more precise measurements, it is customary to lay a transparent goniometer next to the joint to determine this angle. However, problems with accuracy, intra and inter observer variability, are widely known and discussed in the medical literature.

Accurate skeletal information is also vital in performing computer-assisted reduction of fractured bones. The clinical practice of fracture reduction involves the identification of a fracture by X-ray, then the application of reduction principles, some form of fixation to the aligned skeletal segment, and finally, post-reduction X-rays to confirm fracture reduction. The principles of fracture reduction consistently recommend longitudinal traction of the fractured segment while applying corrective forces to recreate the normal alignment of the segment. FIG. 5 illustrates the manipulation of broken bones: femur in FIG. 5A and elbow in FIG. 5B, that can be guided by re-establishing relative alignment of bony landmarks above and below the fracture (by comparing to the other side for example). The normal alignment of the segment is estimated by the clinician, in part by his or her knowledge of anatomy, and to a much greater extent by comparison to the patient's unaffected, opposite side. For some applications, this reduction process is performed under fluoroscopy.

Computer Assisted Tracking Methodologies

The human fingertip (FT) typically has the discriminative tactile ability to distinguish points as near as 2-5 millimeters, depending on the individual, (innate capabilities, degree of training, callous formation, etc.). Various tracking technologies (electromagnetic, optical, or other) exist in the prior art. Examples of such prior art technologies are described in U.S. Pat. Nos. 3,868,565, 3,983,474, 4,017,858, 4,988,981, 5,047,942, and U.S. patent application Ser. No. 2002/0198472, which patents and applications are incorporated by reference herein. Further devices that provide tracking of movements may also be available in the prior art (e.g., the electromagnetic measurement system from Ascension Technology described at www.ascension-tech.com, a measurement system from Polhemus described at www.polhemus.com, and/or the skeleton builder from Motion Analysis Corporation described at www.motionanalysis.com, which information is incorporated by reference herein).

Various types of computer-assisted methodologies may be used in the medical field. For example, references [1]-[31] describe some of the various medical fields that utilize some form of computer-assisted tracking.

However, such prior art methodologies lack numerous beneficial attributes, are not flexible, and have many disadvantages. For example, many prior art devices merely utilize a wand to track movements. Alternatively, prior art devices may not provide the level of granularity necessary in the medical context, and/or fail to allow the flexibility to conduct measurements using real-world movements of an examiner. In this regard, none of the prior art technologies enable or utilize a human user's ability to localize points through touch, position, and pressure sense. In addition, the prior art devices commonly merely deliver tactile information to the fingertip to mimic tactile experience, a field known as haptics in virtual reality technologies. Such mimicking fails to allow the user to freely navigate the real world around them using their own perceptual abilities to assess their surroundings.

Accordingly, what is needed is a device and methodology for tracking an examiner's real-world movements during a medical examination, procedure, and/or therapy.

SUMMARY OF THE INVENTION

The human fingertip has abilities beyond simply localizing a point in space including the ability to discern shape, temperature, and texture among others. One or more embodiments of the invention enable a user to manipulate objects and recreate them in the form of data, numeric or graphical, that gives accurate dimensions. Such data can be used to provide a three-dimensional graphical representation of objects and make some assessment of other qualities of the surface under consideration.

The precise measurements made by a device in accordance with the invention would provide improved data from conventional physical examinations, allowing for more accurate diagnoses, better monitoring of response to therapies, and would provide more consistent data for assessing the outcomes of new therapies. Such measurements could be used to define the standard for office-based medical assessments and obviate the need for more elaborate and expensive out-of-office tests (MRI, ultrasound, X-ray, etc.). Given the financial pressures in the medical industry, the invention may also be utilized by insurers in the form of providing essential data upon which to base reimbursements, before which further diagnostic tests are not authorized.

BRIEF DESCRIPTION OF THE DRAWINGS

Referring now to the drawings in which like reference numbers represent corresponding parts throughout.

DETAILED DESCRIPTION OF THE PREFERRED EMBODIMENTS

In the following description, reference is made to the accompanying drawings which form a part hereof, and which is shown, by way of illustration, several embodiments of the present invention. It is understood that other embodiments may be utilized and structural changes may be made without departing from the scope of the present invention.

Overview

One or more embodiments of the invention provide a simple fingertip tracking device that could be used by physicians during physical exams. Electromagnetic motion tracking sensors can be placed on one or more fingertips, which when calibrated to the user, will communicate position and orientation data of the fingertip to a computer. The tracking sensors may be placed on the distal phalanx of one or more digits by affixing a ring that allows nearly unencumbered positioning of the fingertip(s) to point, probe, palpate, push, pinch, grasp and/or manipulate objects. Such a device would combine the discriminative tactile abilities of the user with the precise measuring and recording abilities of the precision sensors and a computer interface.

An exemplary use allows the examiner to trace an object with an instrumented finger to outline its dimensions precisely. Such a capability allows a dermatologist to map and record the geometry of scars, lesions, and skin features. The same process may be applied to lumps, nodules and masses providing dimensions of height and thickness in a calculation of contour and volume. By grasping two articulating pieces of an object with at least two instrumented fingers on each hand, the user can precisely measure and describe the motion between the pieces. By pushing through liquid or soft substances, the user can measure depth.

To the extent that the computer and software are configured to guide highly organized activities, the fingertip tracker may guide the user in precise manipulation of their fingers or held objects. The human fingertip (FT) typically has the discriminative tactile ability to distinguish points as near as 1-5 millimeters, depending on the individual, (innate capabilities, degree of training, callous formation, etc.). Thus, the invention provides the ability to combine an examiner's tactile ability to localize points and the computer's ability to precisely measure and record position using tracking technologies (electromagnetic). Thus, embodiments are useful in areas where human discriminative skills are most necessary and highly developed, often after extensive training and practice.

Hardware Device

Overview

Figure 6:
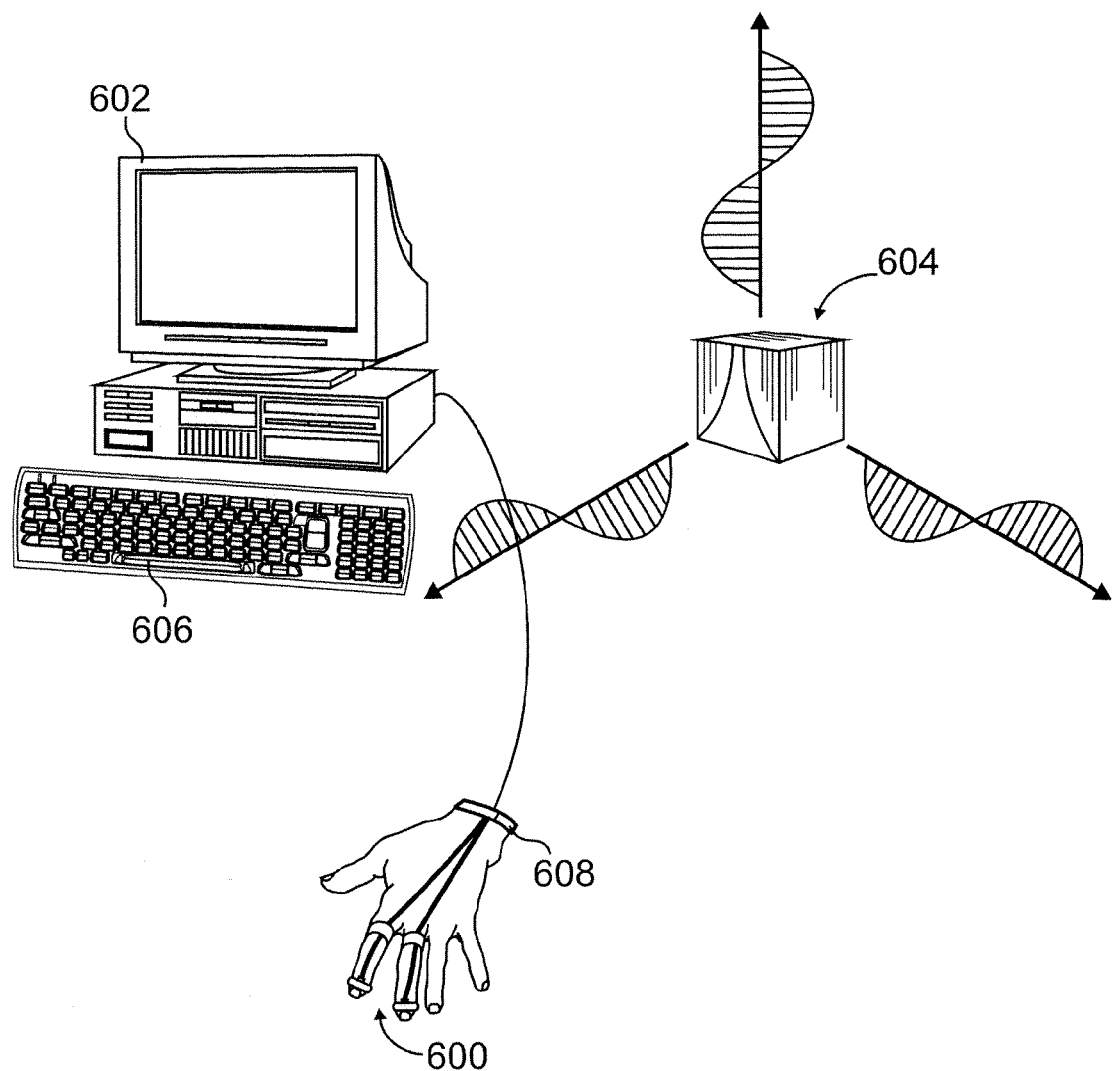
FIG. 6 illustrates the components of a hardware device in accordance with one or more embodiments of the invention.

FIG. 6 illustrates the components of a hardware device in accordance with one or more embodiments of the invention. The hardware device and system provide a means of localizing and tracking one or more of the user's fingertips 600, a central processing unit (CPU) 602 for computation and a means of initiating and terminating the tracking technology 604. The tracking device 600 here is shown as a fingertip-less glove with rings firmly affixed to the distal phalanx. Depending on the tracking technology 604 utilized, there may be external cameras or an electromagnetic signal generator (which are deemed to be incorporated within element 604). The CPU 602 is used for recording data, harboring software protocols, voice recognition technology that may be the means of activating the tracking technology. Otherwise, an ON/OFF switch (that may be controlled as a keyboard 606 on a computer or a footswitch attached to the computer) may be necessary. Data and interactive protocols can be displayed on a monitor or for more limited information a smaller LCD. For example, an LCD screen may be incorporated into the wristband 608 of the fingertip-less glove 600.

Thus, a system/device may contain, or consist of, position and motion tracking sensors 604, which when calibrated to the user, will communicate position and orientation data of the fingertips (FT) 600 to a CPU 602. One or more embodiments fit like a fingertip-less glove 600 with rigid or semi-rigid, ring-like structures securely fitting the distal phalanx of the finger while keeping the FT 600 exposed. Position data may be communicated to the computer 602 by wire or wireless means, either by transducers in the ring-like structures or from surface markers projecting or reflecting to an external optical system 604. Activation of the tracking technology may be done by speech recognition technology in the CPU 602, menu prompts from an interactive monitor or some other ON/OFF switch (e.g., via keyboard 606 or a footswitch).

As set forth herein, various tracking sensors/devices 604 may be used in accordance with the invention. For example, trackers such as those offered under the name of pciBIRD™ or Flock of Birds™ by Ascension Technology may be used. Alternatively, motion capture systems such as that offered by Motion Analysis Corporation (e.g., under the name of Eagle Digital System) may be used. In yet another embodiment, magnetic or other sensors offered by Polhemus™ (e.g., under the name of Patriot™) may be used.

In addition to a fingertip-less glove with sensors, alternative embodiments may utilize a glove (e.g., rubber or otherwise) with or without the fingertips removed. Additionally, to accommodate the invention in a sterile environment, the invention could also be used with a rubber glove enclosing the device and sensors to preserve a sterile field (e.g., external from or internal to a human or living subject).

Figure 7A:
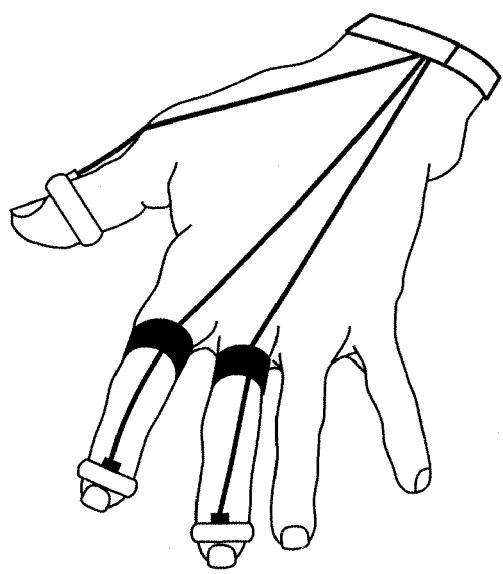
FIGS. 7A-7D illustrate fingertips and sensors in accordance with one or more embodiments of the invention.
Figure 7B:
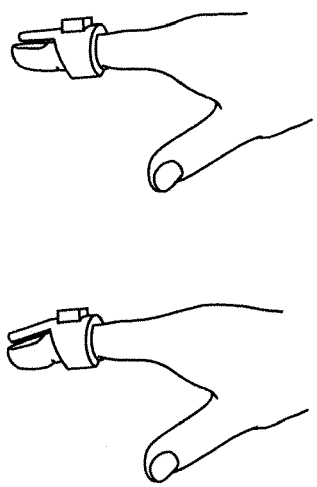
Figure 7C:
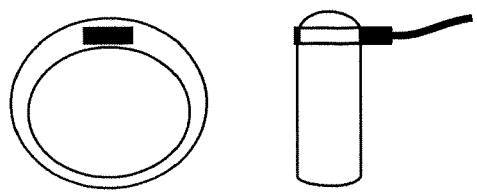
Figure 7D:
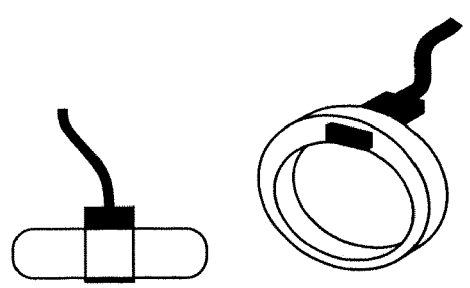

FIG. 7A illustrates an enlarged view of the fingertip-less glove in accordance with one or more embodiments of the invention. Another embodiment may fix one or more of the interphallangeal joints but will still allow tactile probing of the FT 600 with a splint-like device that houses the motion tracking transducer illustrated in FIG. 7B. In yet another embodiment, the distal phalanx of one or more digits may fit like a ring allowing nearly unencumbered positioning of the fingertip(s) to point, probe, palpate, push, pinch, grasp and/or manipulate objects as illustrated in FIG. 7C. FIG. 7D illustrates a front, side, top, and angled view of the ring devices worn on the fingertips 600 as illustrated in FIG. 7A in accordance with one or more embodiments of the invention. Another embodiment that is represented in FIG. 6 by the fingertip-less glove could be implemented in the form of reflective paint or stick-on markers for optical systems.

Depending on the tracking technology utilized, the FT tracking device may require specification of its composition material. For example, electromagnetic tracking technology could require that the device be made of non-metallic material. Similarly, different tracking technologies have different requirements as to how position is referenced to any given coordinate system. For electromagnetic tracking technology, there is a transmitting transducer that may be required somewhere in the examination environment. It may be in a static position, worn by the user or placed somewhere on the object of study. For optical systems, there are usually multiple cameras positioned in the corners of the room to establish room coordinates from which all positions are referenced.

Display of the data to the user will depend on the application and may take several forms. If simple numerical data is all that is required, such numbers may be displayed on an LCD somewhere on the CPU 602, a separate screen or even on an attachment to the FT tracking device worn by the user such as a wristband 608 of FIG. 6. More complex data involving 2-D and 3-D graphical output may be displayed on a separate monitor communicating with the CPU 602. For some applications, the data presented may be purely positional in which cases the graphic display will mostly represent some projection of a coordinate system of the examination space. The accumulated data will reflect various paths of the FT in this space.

Other applications involve varying degrees of interpolation such that the graphic presented may make extensive assumptions about the task underway or the data collected. For example, if the task is measuring and making a representation of the tibia bone, then palpating several discrete points, such as the tibial tubercle near the knee and the malleoli of the ankle, may result in the depiction of a well constructed tibia bone that is merely scaled to match the physical dimensions of the selected points. In one sense, some of the data so presented is an assumption or even fictitious. In another sense, this graphical method informs an educated observer about the task underway and the data collected. Accordingly, an entire skeleton can be created in this manner, one that is largely representational but with very detailed and specific information with respect to the dimensions and proportions of the subject under study.

In another embodiment, the display of data could be provided through augmented reality goggles worn by the user showing the position of their FT(s) in relation to schematic data of the external world while allowing visualization of the external world at the same time. For example, an orthopaedic surgeon with a finger in a patients shoulder contacting a certain point of the anatomy will feel that point, see it with his/her eyes, and simultaneously see where that point relates to a previously obtained imaging study of some kind (MRI or CT).

Figure 8:
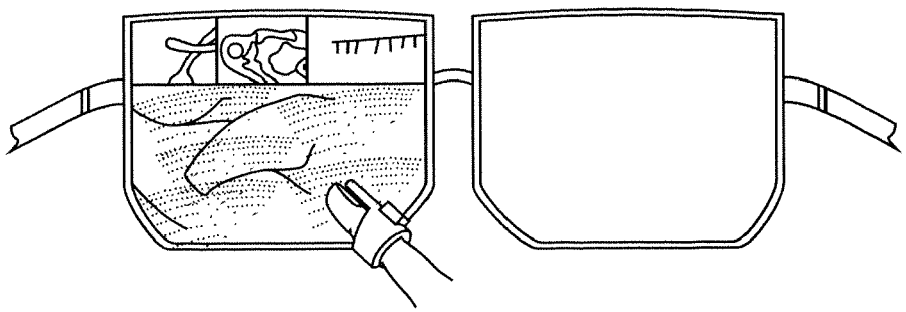
FIG. 8 illustrates an example of augmented reality goggles assisting in surgery on the clavicle in accordance with one or more embodiments of the invention.

FIG. 8 illustrates an example of such augmented reality goggles showing an application in surgery in which the plain X-ray, a CT scan, and related post-surgical example are depicted in small monitors while allowing the surgeon to view the surgical site and instrumented fingertip 600. Some portion of the goggles may be devoted to the presentation of either acquired or manipulated data so that this information is available to the user in real time. In the example shown, the upper one third of the visual field is devoted to three independent small monitors, each showing different but related information. This may be three different projections (e.g. AP, lateral and transverse) of a relevant imaging study serving as a coordinate system that localizes the position of the FT 600. These small monitors could be anywhere in the visual field and could be devoted to any relevant body of graphical information.

Fingertip Tracker Mounts

The description above provides an overview of the components of a fingertip tracker device/system in accordance with one or more embodiments of the invention. In addition the above-described components, embodiments of the invention may utilize fingertip tracker mounts.

Figure 9A:
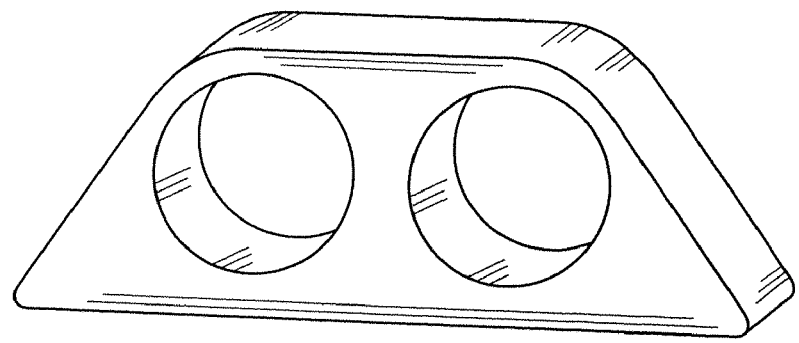
FIGS. 9A-9C illustrate finger sensor mounts in accordance with one or more embodiments of the invention.
Figure 9B:
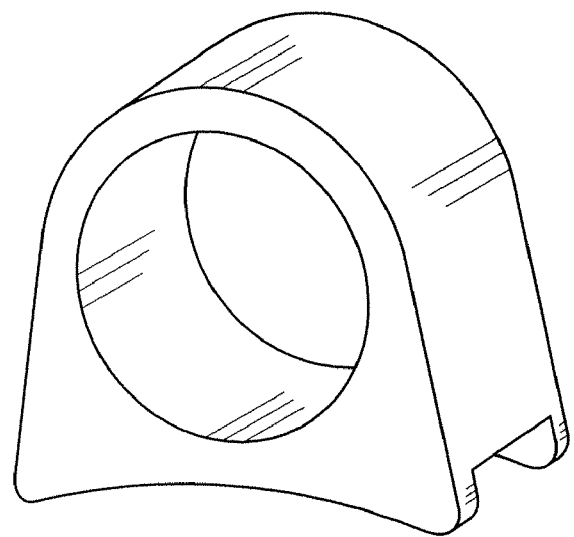
Figure 9C:
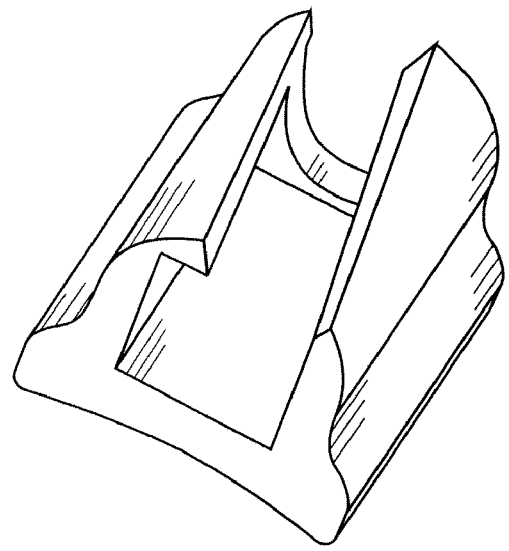

Several components make up the mount system. Referring to FIGS. 9A, 9B, and 9C, a wrist cord holder (FIG. 9A) (e.g., attached to a wristband 608) and a finger cord holder (FIG. 9B) keep the cords in line in order to reduce the tension on the sensor. The finger sensor mounts (FIG. 9C) hold the sensor to the user's finger. An additional, optional ring may slide over the tip of the finger to help a user repeatedly identify the same spot on his/her finger.

The intent of the wrist cord holder of FIG. 9A is to alleviate strain on the cord (which would cause the sensor to be unstable). Various different designs may be utilized in accordance with the invention. In one embodiment, both cords could be held together. However, such a design may be problematic because the cords could stick to each other during movement. An alternate embodiment provides a snap in slot so that the cords can fit inside. In such an embodiment, the holes must be properly sized to allow the cords to move easily. Additionally, because the wrist mount is likely to have the most tension on it (since the wrist mount is closest to the long cable that attaches to the CPU 602), it is likely that the cords may pop out or remain stuck in one of the snap slots. In a third embodiment illustrated in FIG. 9A, two tunnel-like tubes are provided. A flared end provides the ability for the cord to pass through at an angle. Additionally, each tube/hole may be more than twice the diameter of the cord itself so the sensor and cord can easily slide through.

In addition to the wrist mount itself, various designs may be utilized for the "bracelet" 608 that the wrist mount attaches to. For example, simple hook and loop fasteners (e.g., Hook and Loop Fasteners™) and elastic could be used. However, such a design may take too much coordination/too many hands to securely fasten the bracelet 608 and wrist mount to the user's wrist. An alternate embodiment may utilize foam, hook and loop fasteners, and elastic combination. Such a design may only require a single person to pull the elastic through the hook and loop fasteners and press it on.

In very much the same way as the wrist cord holder of FIG. 9A, the finger cord holder of FIG. 9B is designed to alleviate strain on the cord. Similar to the wrist cord holder, the finger cord holder of FIG. 9B has one tunnel-like tube per finger affixed to a foam-hook and loop fastener-elastic combination ring.

The finger sensor mount of FIG. 9C must be small and low profile enough to accommodate the placement of the sensor inside/under a medical glove. In addition, the finger sensor mount must be sturdy, relatively comfortable, and very secure. In one or more embodiments, a Pugh chart may be used to determine the ring, mount, and stabilization designs for creating a clay mount prototype. Various problems with ring mount design include poor ease of attaching to the ring, internal lining sticking to itself and subsequent inability to insert the sensor, and a high likelihood of the sensor pulling out or moving within the mount. An alternate embodiment may utilize a plexiglass mount. However, without the use of a rapid prototyping machine or micromachining tools, plexiglass mounts may be bulky and difficult to use. Further, plexiglass may protrude far above the finger thereby subjecting the sensor to additional movements (even if the mount itself maintains a perfectly rigid sensor). Additionally, having multiple parts (lid, screws, etc.) makes it more difficult to assemble and more likely to break.

In view of the above, various different finger sensor mounts may be created with a rapid prototyping machine. For example, a press fit may be utilized. Alternatively, a press fit mount may be created with a lip. Such a lip allows the sensor to slide over and then lock into place. However, to remove the sensor from such a mount, the user may be required to pull on the cord, which could damage the sensor or cables. Additionally, the lip on the bottom may necessitate a larger cavity for the sensor to move in, making it less secure. A third embodiment provides for a slit assembly, wherein a slit is added to the top of the mount so that the cord could snap through, thereby eliminating any pulling on the cord/sensor. However, it may be problematic to perfect the size of the slit. In this regard, if the slit is too large, the ring may not hold the sensor in place securely, but if it is too small, the cord may not fit through (e.g., a cord diameter of 4 mm as compared to a sensor width of 5 mm). A fourth embodiment provides a lid assembly wherein a mount has a lid that snaps or slides on. However, it may be problematic to make slots of the appropriate size to accommodate the lid. Further, the lid is more likely to get lost or stuck if it is not attached completely.

An alternative embodiment provides for utilizing a modified slit assembly. To increase the ability of the mount to hold the sensor on both sides of the top and to allow for a wider slit (for easier cord insertion), the slit may be diagonal, with a slight increase in size toward the distal end. FIG. 9C illustrates such a diagonal slit assembly in accordance with one or more embodiments of the invention.

In addition to the mount itself, various styles of rings may be utilized. A first ring style may be determined from a Pugh Chart. Such a design involves a combination of a solid mount, an elastic band, and hook and loop fasteners to affix the elastic. However, such a ring may be difficult to operate and/or require too much coordination/too many hands to place on the finger.

A second ring style is a hook and loop fastener slip through. In such an embodiment, hook and loop fasteners are affixed to the mount and elastic is constructed to slide through the hook and loop fasteners. The elastic sticks to the hook and loop fasteners. Thus, a reduced amount of coordination is necessary to secure the ring.

A third ring style is a hook and loop fastener slip with fat ring. In such an embodiment, a ring that is wider than the hook and loop fasteners is utilized to provide more stability and distribute the compression (of a tight ring) more comfortably.

A fourth ring style is a hook and loop fastener slip with foam ring. In such an embodiment, the foam provides for a ring that is sturdy, stable, and comfortable.

A fifth ring style is a hook and loop fastener with metal tab. Such an embodiment has an elastic slip under a bar affixed to the mount that is secured/stuck to the hook and loop fasteners. However, due to the small size in such a device, adjustment of the elastic may be difficult since the elastic may adhere to the hook and loop fasteners while moving under the bar.

As described above, an optional placement ring or extension may be used to help a user find the same spot on his/her finger many times in a row. To the extent that this ring or extension is rigidly fixed or adherent to the user's fingertip and readily detectable, this will enhance the precision of point localization. To the extent that this ring or extension is rigidly fixed to the sensing transducer, so long as it's position is readily ascertainable by the user's fingertip, motion artifact between the fingertip and transducer will be minimized. Embodiments of an optional placement object consisting of a ring or extension that contains/comprises a nub or a hole.

Figure 11:
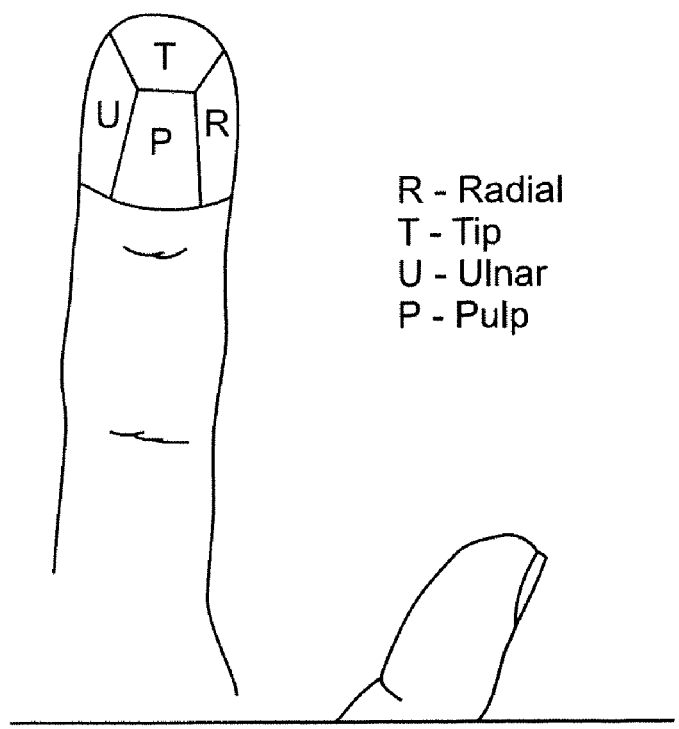
FIG. 11 illustrates the different regions of a fingertip that may be used to perform complex activities in accordance with one or more embodiments of the invention.

Various different methods may be used to create a nub on the placement object. Referring to FIG. 11, the numb may be placed on any of the regions U, T, P, or R. In one or more embodiments, the nub is placed on the pulp (P) or tip (T) of the finger.

For example, a thin elastic ring or extension may have a dollop of glue to help the user feel a particular point on the finger. To secure the elastic, the elastic may be attached to a hook and loop fastener strip that can be stuck to the sensor mount itself. However, the glue may be very hard for the user to feel. Accordingly, two strips of elastic that intersect may be used. Such an embodiment may not be flexible/adjustable, and the elastic may roll off the user's finger if the finger is too large.

In a second nub embodiment, a small "nub" is glued to the elastic. However, such an embodiment has limitations similar to those described above, may be uncomfortable, and can be difficult to construct.

In a third nub embodiment (referred to as a balloon, foam nubs), a small strip of balloon (or the material a balloon is made of [eg: latex or nitrile]) may be connected to make a ring that prevents slipping and rolling. The nubs may be created from softer foam materials. Though the balloon may cure problems noted above with respect to the elastic, the nubs may be too soft to be consistently felt.

A fourth nub embodiment (referred to as a balloon, hook and fastener nubs) provides for balloon strips that are outfitted with small pieces of hook and loop fasteners.

A fifth nub embodiment may provide for balloon rings that have small beads glued to them.

Hole prototypes may also differ in various respects. In a first hole embodiment (referred to as a hard ring), a ring of metal having a hole may be used. However, such a ring may be uncomfortable and too thick for the finger to actually hit a surface. Additionally, metal may interfere with the sensory equipment. Alternatively, a thin clay ring may be used. However, while a clay ring may be more comfortable, it may be insecure and tend to stretch.

A second hole embodiment (referred to as a balloon, elastic ring) provides for the construction of a hard secure ring wherein strips of balloon are secured/glued to hardened elastic. Though these rings may be strong and remain secure, the hole may be not felt. Further, if the user has large fingers, the holes in the rings may increase/expand and become imprecise.

A third hole embodiment (referred to as a spandex ring), a ring may be made using a thinner or synthetic fiber material such as spandex/elastane (i.e., to increase the feeling sensation). In such an embodiment, glue (e.g., superglue) may be necessary around the holes to maintain the size of the holes. However, such glue may increase the thickness of the rings thereby making the rings both uncomfortable and difficult to feel through.

A fourth hole embodiment (referred to as a spandex/balloon ring without glue). Without glue, discerning the hole from the ring may be difficult. Accordingly, balloon, a thinner material, may be used. However, the hole in such a ring may also be difficult to discern. Additionally, the hole may expand when used on larger fingers.

The fingertip tracker rings may be created in a variety of ways. Once such methodology is described herein. A pattern may be created for the ring. Thereafter, black foam and hook and loop fasteners (e.g., ¾ inch) may be cut in accordance with the patterns (e.g., using a scissors on the foam and razor blade on the hook and loop fasteners by cutting on the plastic surface). Elastic (e.g., ¼ inch and ½ inch) may then be cut (e.g. using a scissors) according to the length needed. Plastic parts formed from stereolithography may then be glued to one end of each foam strip. In this regard, the finger mount and finger cord holder should be the same width as their foam strips. The wrist plastic element should be centered on the foam strip. The elastic may then be glued to the other end of the foam strip. In this regard, the elastic should be centered and provide at least ¼ inch to securely bond. Additional glue may be used on the elastic to reduce any potential for fraying. The hook and loop fastener strips may then be glued to the sides of the mounts and the elastic may be threaded through the hook and loop fasteners.

Alternative fingertip mounts may also be used in accordance with the invention. For example, a glove could be used. In another example, a finger wrap such as a wrap that attaches only the sensor mount and the finger cold holder may be used.

Fingertip Tracker Setup

Once the devices are created as described above, the devices must be placed on the user/examiner's hand. One or more embodiments of the invention utilize two sensors per hand (e.g., on the thumb and either first or middle finger). The sensors are attached to a ring and the cord threads through two additional rings to reduce the tension on the sensor. An additional, optional ring can be worn over the very tip of the finger (as described above) to help a user repeatedly identify the same spot in his/her finger. To place the sensors on the user's hand, the following sequence of steps may be utilized. For purposes of this description, the fingertip tracker mounts and construction described above will be used.

First, if the sensor is not already affixed to the ring mount, the cord may be snapped through the slot on top of the ring mount and the sensor slid back into the mount until it cannot slide any further. The cords may then be threaded through the knuckle cord holders and then through the wrist cord holder. Different systems may be utilized for the "left hand" and the "right hand" (differing in the ring orientation with respect to the sensor). The user should ensure that mounts for the same hand are attached.

The second step is to slip the wrist cord holder on and tighten by pulling on the white elastic strip. While the elastic is still extended, it should be pressed against hook and loop fastener to properly secure it. If the user has a smaller wrist, the end of the elastic may be secured with a hook and loop fastener strip on the opposite side of the holder.

The third step is to place the knuckle cord holders on the fingers and tighten by pulling on the white elastic strips. While the elastic is still extended, the elastic may be pressed to the hook and loop fastener to secure. If the user has smaller fingers, the end of the elastic may be secured with a hook and loop fastener strip on the opposite side of the holder.

The fourth step provides for putting on the sensor mount rings and tightening them by pulling on the white elastic strips. While the elastic is still extended, the elastic may be pressed to the hook and loop fastener to secure. If the user has smaller fingers, the end of the elastic may be secured with a hook and loop fastener strip on the opposite side of the holder.

For the optional ring, the ring may be pulled on and positioned securely such that the bump is over the preferred spot on the finger.

Device Training/Calibration

Once the device is properly placed on the user's/examiner's hand/fingers, the device should be calibrated to localize the position of the user's fingertips. A calibration process with statistical sampling will allow for, and define, the range of variability for any given user.

Figure 10:
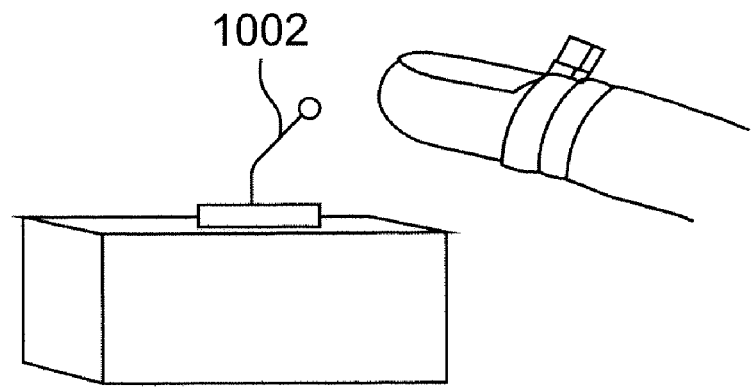
FIG. 10 illustrates the calibration of a known point in accordance with one or more embodiments of the invention.

Several methods may be used for calibrating the device. One method for calibration is illustrated in FIG. 10. With FT tracking technology in place, the user may contact a 2 mm target (e.g., a pin head 1002) with a known location against the area of the fingertip to be used for a given application. The training aims to ensure both that the user reproducibly engages the same region of the fingertip and applies a consistent force to achieve the same depth. The soft pulp of the fingertip usually allows for one to a few millimeters of compression depending on how hard the user pushes. Using the user's own pressure sense and proprioception, the user can learn through this calibration process to apply a consistent pressure or to distinguish between high pressure and low pressure states for different measurements.

The user can either learn to use one region of the fingertip consistently or learn to recognize different regions of the same fingertip for more complex activities. FIG. 11 illustrates the different regions of a fingertip that may be used to perform complex activities. The fingertip has the ability to discriminate points as close as 2 mm. Practically, the area of the fingertip that is used is activity dependent. For activities in which the thumb opposes one of the fingers, the ulnar (U) aspect of the thumb presses against the radial (R) aspect of the finger. For other activities, the user may preferentially engage the tip (T) of the finger. For many other activities, the user engages the most central, fleshy area of the fingertip referred to here as the pulp (P). Embodiments of the invention provide that the user begin with a training protocol to reliably identify regions within these four areas of the fingertip that are less than 5 mm in diameter. Depending on the application and the innate ability of the user, these regions may be further subdivided and localized.

Implied in this calibration process is the establishment of a coordinate system for the examination space, which again depends on the motion tracking technology selected. If a system that is based on the coordinates of the room is in use (such as an optical system), then specific points on the subject under study must either be identified and tracked for reference or the subject must remain static. Similarly, if a system that requires positions be referenced to a transmitter is in use (such as electromagnetic), then either specific points on the subject under study must be tagged with position tracking elements and be tracked for reference or the subject must remain static. In this instance, there is the added possibility that the subject houses the transmitter in a defined place that does not confound measurement of any other moving parts.

Figure 12:
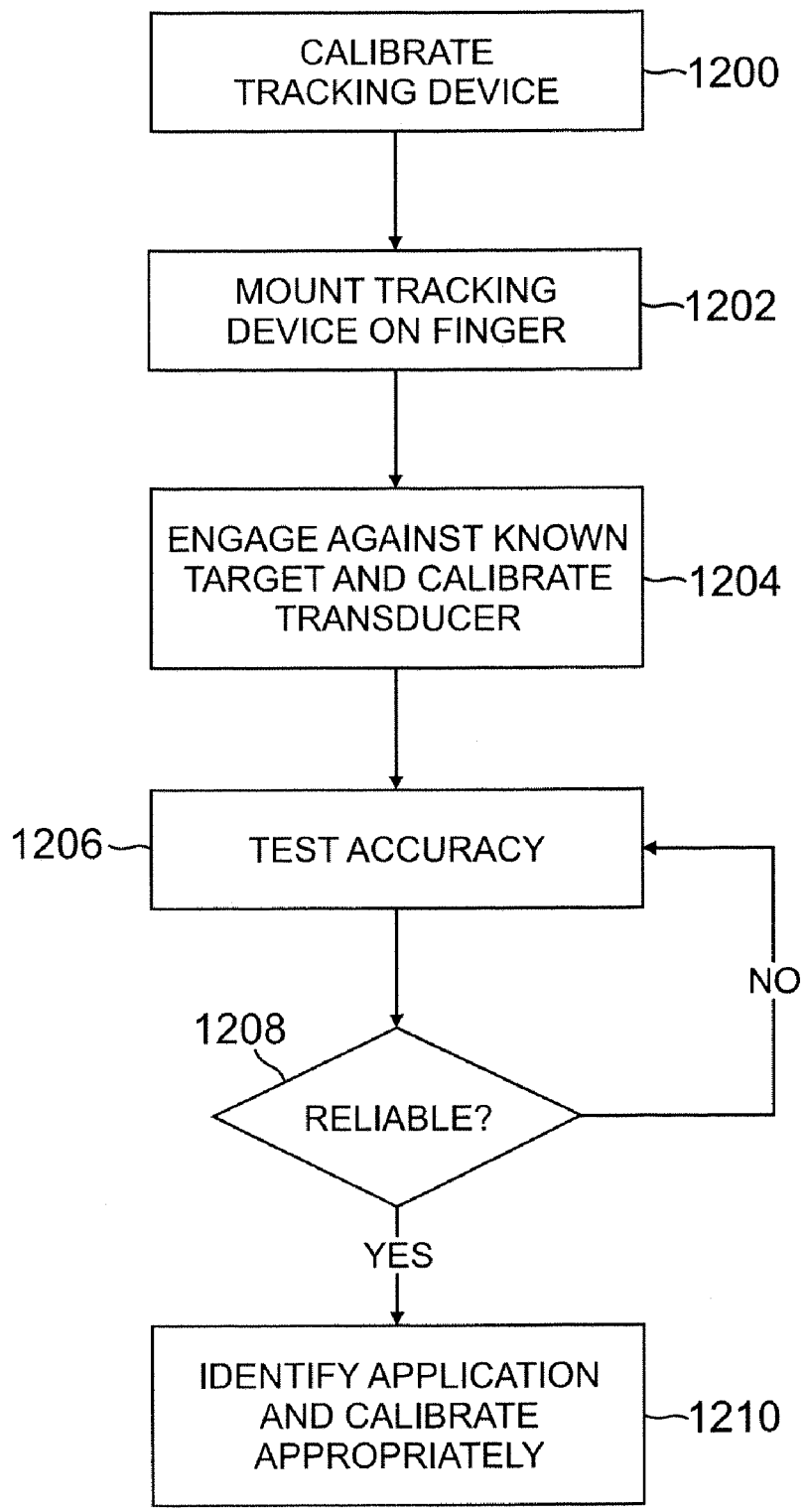
FIG. 12 is a flow chart illustrating the protocol for performing the training/calibration process in accordance with one or more embodiments of the invention.

FIG. 12 is a flow chart illustrating the protocol for performing the training/calibration process in accordance with one or more embodiments of the invention. At step 1200, the tracking device is calibrated to a local coordinate system depending on the tracking technology. At step 1202, the tracking device is mounted on the finger (e.g., as described in detail above). At step 1204, the fingertip with the tracking device is engaged against a known target (size, location, etc.) and the transducer is calibrated to recognize the position of the fingertip.

At step 1206, testing is done to determine the accuracy of the fingertip position with respect to intended objectives. In other words, a determination is made regarding whether the sensor on the fingertip touches the known point within a defined threshold. Such a threshold may be pre-defined by the system based on the intended objective, may be dynamically defined by the user, may be defined by a third party (e.g., via an application programming interface (API) of the software), or defined via an alternative mechanism.

At step 1208, a determination is made regarding whether the testing at 1206 was reliable and consistent with the intended objectives (or within the defined threshold). If unreliable (or outside of the scope of the defined threshold), the testing is repeated until the user reliably positions the fingertip against target to an accuracy consistent with intended objectives (i.e., within the defined threshold). Such a testing/training process may be facilitated by use of contact paper or other methods that help the user identify and locate the specific position of fingertip reproducibly. For some applications, the orientation of the fingertip may be important. For others, the point of contact irrespective of the angle at which the fingertip makes this contact, will be all that is important. Depending on the application, the software interface will either provide orientation data or eliminate it.

Once reliable, the process continues at step 1210 where the application is identified (e.g., as a localization, tracing, etc.) and calibrated appropriately in accordance with an appropriate procedure.

The calibration and training of the fingertip tracking technology may be developed to achieve basic or complex goals. Basic goals may aim to reproducibly identify a 5 mm region within the fingertip pulp. Complex goals may add to this aim: (1) identifying multiple adjacent regions of the same fingertip; (2) specifying the depth that accompanies different amounts of pressure (distinguishing light touch from deep pressure); (3) fine tuning target regions to within 2-3 mm or within the sensory capacity of the user; (4) instrumenting multiple FT's of the same hand; and/or (5) instrumenting both hands.

As an example of using the fingertip tracking technology, the user may have one or more fingers instrumented while the computer tracks multiple regions and depths of each fingertip. Depending on the application, the user reads from the data most applicable. Thus, if the radial region of the index finger contacts an object of interest that also contacts the ulnar region of the thumb, the position of each are known. Distance, orientation, and motion of these two points may then be easily calculated.

A second calibration/training method is described below. Fingertip tracking software is installed and configured to execute on CPU 602. Such software may prompt the user through a series of steps to configure and calibrate the device. Initially, the software is started up and position data may be corrected using a best-fit calibration function. Such position data may be provided to improve the accuracy of the sensors. In this regard, the accuracy of sensors may be indicated by a sensor provider to be approximately +/−1.8 mm RMS. However, upon examining the data returned by sensors, it may be found that the error in accuracy for the unadjusted data is closer to 3.6 mm RMS. By applying an appropriate corrective function (e.g., a set of mathematical operations on incoming sensor data), the accuracy of the devices may be improved. For example, by performing least-squares fits with various functions, the accuracy of the devices can be improved to 1.8 mm RMS or better.

To provide the data correction, a test bed for the sensors may be utilized that consists of a flat table with a grid of holes every two inches to accommodate the sensor. Measurements in the z direction may be accomplished by constructing a structure that holds the transmitter at precise heights (e.g., within defined accuracy tolerances). For example, a sensor may have an indication (e.g., by the sensor provider) that the operational range of the device is a 76.2 cm radius about the transmitter. Thus, data collection may be confined to be within this range. The data points may then be recorded throughout the frontal hemisphere (positive x) with respect to the transmitter.

The data collected from the device may then be processed into Matlab™ for analysis. Analyzing a typical layer of data points in Matlab™ may reveal similar trends in the error of the points in the z direction. In this regard, each layer may exhibit the same curvature, with a relative maximum near the center and diminishing accuracy closer to the fringes of sensor range. The ideal correction to this data would be a mapping from the curved, raw data to a flat plane. To accomplish this, a least-squares fitting function may be used for correction in the x-, y-, and z-directions. However, instead of operating in one or two dimensions, the data points from the sensors vary in all three dimensions. For every point, there is an associated x-, y-, and z-error. In other words, each reported point, (x, y, z), represents an actual spatial (X, Y, Z) point. The least-squares fitting maps a set of input points to an output value. Having three-dimensional error requires three corrective functions that each depend on the reported (x, y, z):

$$X_e(x,y,z)=f_x(x,y,z)$$

$$Y_e(x,y,z)=f_y(x,y,z)$$

$$Z_e(x,y,z)=f_z(x,y,z)$$

where $X_e, Y_e, Z_e$ are the estimated spatial coordinates based on a given sensor input, (x, y, z). The corrective functions, $f_x, f_y, f_z$, are produced through the least-squares method and depend on the choice of an approximating function.

The shape of each layer of data points provides an indication for types of approximating functions to use. Starting with a second-order general polynomial of the form:

$$a0+a1z+a2z^2+a3y+a4yz+a5y^2+a6x+a7xz+a8xy+a9x^2$$

the least-squares method may be used to determine the coefficients, $a_n$, that provide the best correction for sensor data. While such a methodology may improve accuracy, the sensor data at the extremes may have the most errors. Accordingly, additional functions may be tested including higher-order polynomials, trigonometric, exponential, and hyperbolic trigonometric functions. An additional/alternative corrective function involves the use of the second order function shown above, as well as a collection of hyperbolic sine and cosine terms to account for the increased error for larger distances from the transmitter. Accuracy may be further improved by treating the data in sections rather than dealing with the entire set of data points.

In view of the above, the corrective functions may be viewed as a set of mathematical operations performed on the incoming sensor data. Implementing the functions may involve adding a module to software of the invention that alters the output x, y, and z values accordingly. Because of the simplicity of the corrections, no noticeable computational loss may occur, even with multiple, layered correction functions.

The least-squares method corrects the raw sensor data based on precisely recorded points. However, because the correction depends heavily on the quality and accuracy of the calibration process, any change of environment may impact the validity of the data correction. The amount of error coming from the sensors varies with several factors including the inherent noise of the device and operating environment. Certain sensors may be particularly sensitive to metallic objects in close vicinity, and great care should be taken to minimize or eliminate metal in the test setup. As such, a particular corrective function may only be valid for specific setups where the device is utilized/tested. In this regard, if a device is moved to another testing location, such as a clinician's office, the sensor readings may change, requiring a recalculation of the corrective functions.

Also, if a new transmitter is used, the sensors may have to be recalibrated and resulting corrective functions reevaluated. Overcorrection may occur if the data sets chosen are too small. That is, if there are fewer data points than there are coefficients to solve for. In one or more embodiments, final correction functions may consist of 16 unknown coefficients to solve for. Accordingly, while the sample size of points is greater than 16, overcorrection does not occur. However, it may be beneficial to include more sample points than variables to solve in order to account for measurement error. Thus, more points may have the effect of "averaging" out outlying data that is a result of measurement error.

In addition to the above, it may be possible to greatly improve the accuracy past an RMS error of +/−1.8 mm. The nature of the data points is fairly well-behaved. In this regard, there are no points that drastically deviate from neighboring points. With the exception of areas near the extremes of the operational range of the device, the points for each layer are very smoothly distributed. One may take advantage of this distribution by reducing the sample size of points for each set of correction functions. Instead of introducing errors from overcorrecting, the resulting correction functions would almost perfectly match the warping caused by the sensors. This increase may come at the cost of increased computation since there may be an increase in the number of logical tests needed to determine the correct set of correction functions for a particular input. Alternatively, a massive lookup table of input points and a corrected point may be constructed. Thus, all answers can be pre-computed, and the only computational requirement may be a constant time memory look-up.

Figure 13:
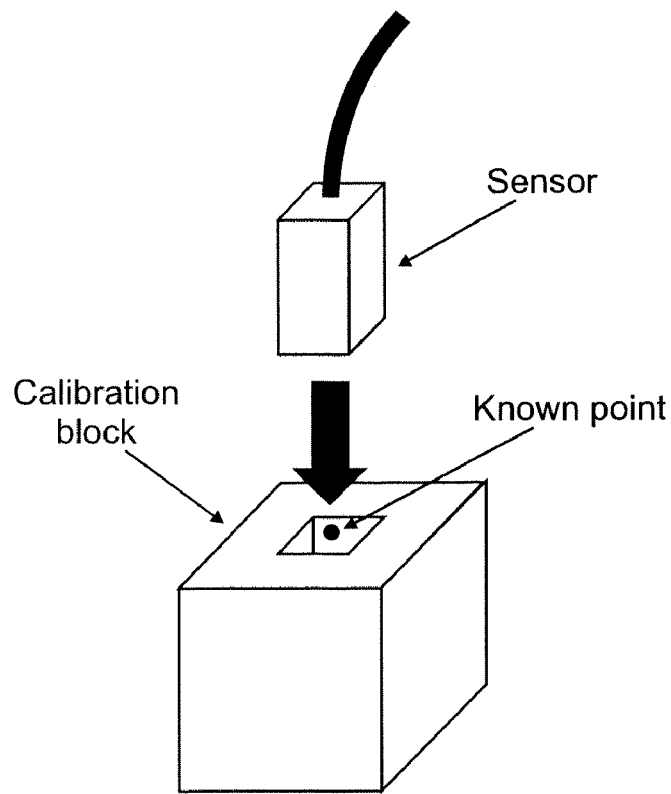
FIG. 13 illustrates the determination of a known point through placement of a sensor into a calibration block having a known point in accordance with one or more embodiments of the invention.

Subsequent to data correction, the user may be prompted through a process for calibrating the sensor of the device using known points. Accordingly, the user may initially be directed to determine the location of known points by inserting each of the (4) sensors (i.e., before placing the sensor on the fingertip) into a calibration device. Once inserted, the user may save the coordinates of the sensors in the software system (e.g., by clicking an OK button in a dialog). Once saved, the location of four points in space is known. FIG. 13 illustrates the determination of a known point through placement of a sensor into a calibration block having a known point in accordance with one or more embodiments of the invention.

Figure 14:
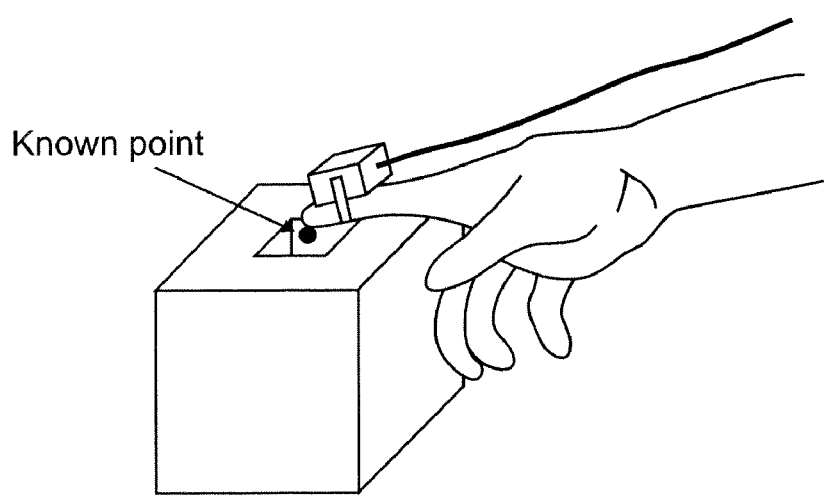
FIG. 14 illustrates sensors attached to fingers and a calibration of the sensors in accordance with one or more embodiments of the invention.

Once the points are known, the device may be calibrated to the known points. As illustrated in FIG. 14, the sensors are attached to the fingers, and the four previously determined known points are touched (and the movement recorded). Thereafter, the coordinates of the known points are subtracted from the coordinates of the sensors on the fingers, giving a vector pointing from the sensor to the known point at the fingertip. A rotation matrix determined from the orientation angles of the sensor relative to the transmitter fixed reference frame is multiplied by this vector to rotate the vector back into the transmitter's reference frame, and saved to memory as a calibration vector. In all subsequent measurements, the inverse of the rotation matrix determined by the orientation angles of the sensor is multiplied by this calibration vector to rotate the vector into the sensor's moving reference frame, and then added to the coordinates of the sensor to account for the position of the fingertip.

Thus, as described above, the three steps in calibrating the device provide for data correction, determining a known point, and then calibrating to the known point.

Application Overview

Once calibrated, the device may be used in a variety of contexts. In the most general sense, the purpose of the device is to combine the proprioceptive abilities and skill of the user with the precise measuring and recording abilities of the computer interface. By tracing an object with an instrumented finger, the user can outline its dimensions precisely. By grasping two articulating pieces of an object with at least two instrumented fingers on each hand, the user can precisely measure and describe the motion between the pieces. By pushing through liquid or soft substances, the user can measure depth. To the extent that the computer and software are configured to guide highly organized activities, the fingertip tracker may guide the user in precise manipulation of their fingers or held objects. Descriptions of general applications are listed below.

Measuring Application

One specific application is to define the distance between two points. One fingertip is placed in contact with a point of interest. Either the same fingertip sequentially, or another fingertip either on the same hand, the thumb, or the other hand or even from another instrumented user, is placed on another point of interest. The distance between the two points of interest is then calculated. The limits of the measurable distance are determined by the reach of the user and the tracking technology employed. For these purposes, distances within the reach of the user and/or another user in the same room are applicable and consistent with available electromagnetic and optical tracking technologies.

Figure 15:
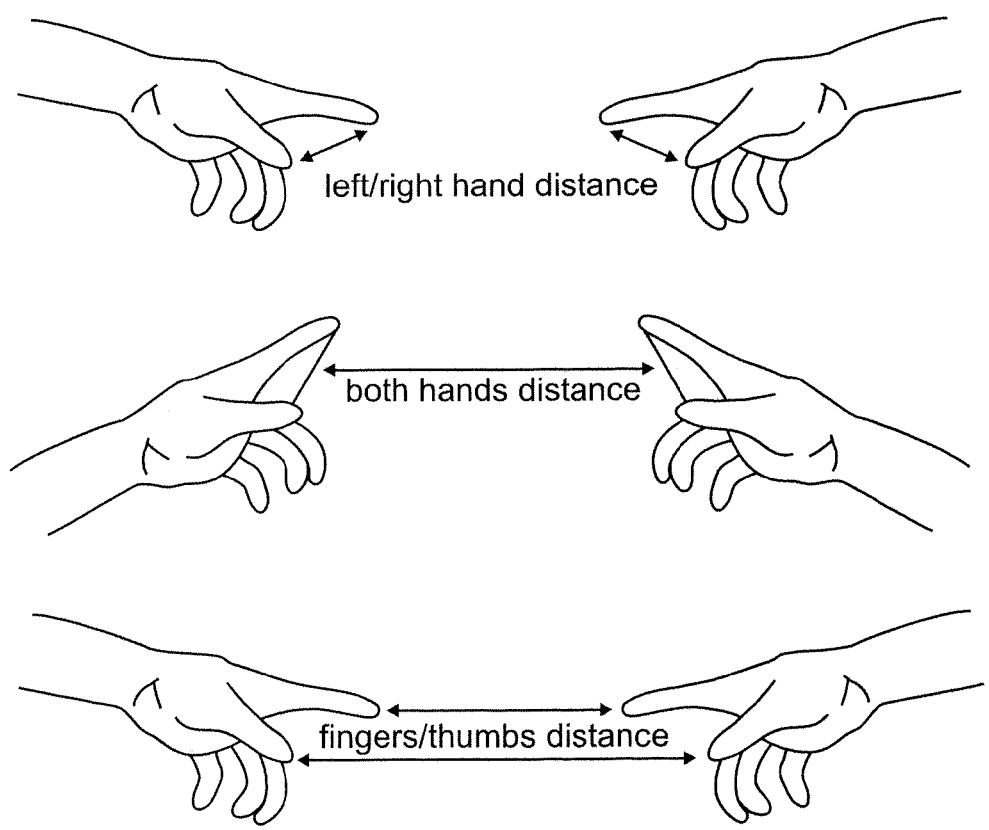
FIG. 15 illustrates the various distance calculations that can be measured in accordance with one or more embodiments of the invention.

FIG. 15 illustrates the various distance calculations that can be measured in accordance with one or more embodiments of the invention. The right hand distance refers to the distance between the two sensors on the right hand, i.e. from the right thumb to the right finger. The left-hand distance refers to the distance between the two sensors on the left hand. "Both hands distance" refers to the distance between the midpoint of the two sensors on the right and left hand, i.e. from the midpoint of the right thumb and the right finger to the midpoint of the left thumb and the left finger. The "fingers distance" refers to the distance between the two sensors on the left and right fingers. The "thumbs distance" refers to the distance between the two sensors on the left and right thumbs.

Figure 16:
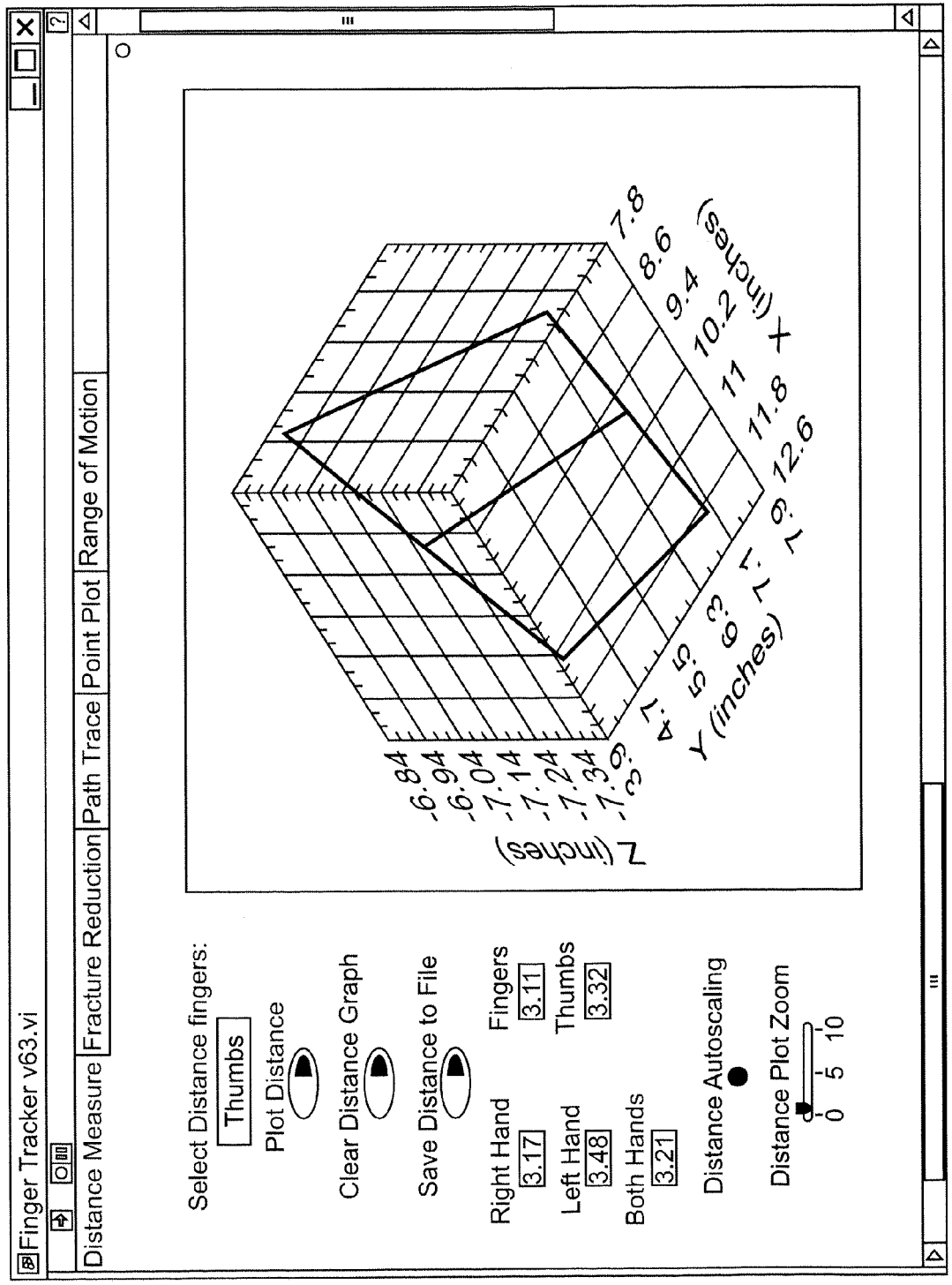
FIG. 16 illustrates a plot of distance measurements in accordance with one or more embodiments of the invention.

As illustrated in FIG. 16, the different distances can be plotted on a coordinate system in the form of pairs of points, connected by a line, corresponding to the sensor coordinates and a specified distance (e.g., via a pull-down menu). Users may also have the option to clear the distance plot, or save the distance plot to a file (wherein the array of distance point pairs that have been plotted are saved to a user-specified file). Field in the display window of FIG. 16 display the various measured distances. In addition, the user may autoscale the distance plot, enable zooming, and/or adjust the (x,y,z) scale of the distance plot.

Path Trace/Contour/Volume

Embodiments of the invention may be utilized to define the linear size and shape of an object of interest. To define the size and shape, a fingertip may be placed at some point along a line of interest. The tracking technology is initiated as the finger traces, either continuously or discontinuously, along the line of interest. When the end of the point of interest is reached, the tracking function may be terminated.

Similar to tracing, the size, shape, and surface characteristics of an object of interest may also be defined using a contour. To utilize such a contour, the user begins by defining or tracing the linear boundaries of the surface to be evaluated. Thereafter, the instrumented fingertip is passed back and forth over the surface of interest while attempting to touch enough representative points to represent the surface.

In addition, the user may desire to define the volume of an object of interest. The procedure is similar to that for tracking and contour analysis as described above. However, the software may also be configured to perform a calculation of the volume enclosed by either multiple tracings or under the surface of a selected contour.

Path tracing may be conducted in a variety of manners. In one or more embodiments, the user may be enabled to identify the individual sensors (e.g., right finger, right thumb, left finger, and/or left thumb) that is used to plot path data. When used in a path trace environment, the terms Right Finger, Right Thumb, Left Finger, and Left Thumb refer to the individual sensors for which the user wishes to plot path data. Right Hand refers to the midpoint of the two sensors on the right hand, the path of which will be plotted. Left Hand refers to the midpoint of the two sensors on the left hand, the path of which will be plotted. Both Hands refers to the midpoint of the two sensors on the right and left hand, the path of which will be plotted. Fingers refers to the midpoint of the two sensors on the right and left fingers, the path of which will be plotted. Thumbs refers to the midpoint of the two sensors on the right and left thumbs, the path of which will be plotted.

Figure 17:
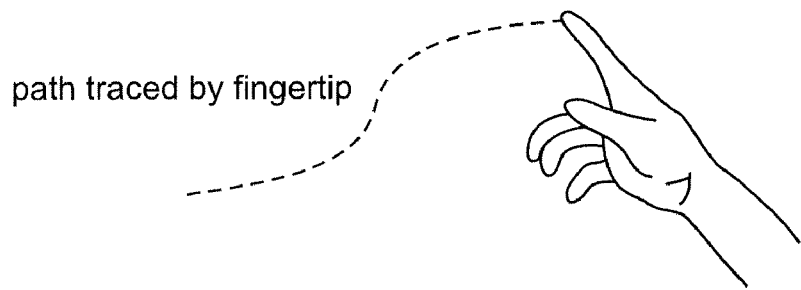
FIG. 17 shows the path traced by a single fingertip in accordance with one or more embodiments of the invention.
Figure 18:
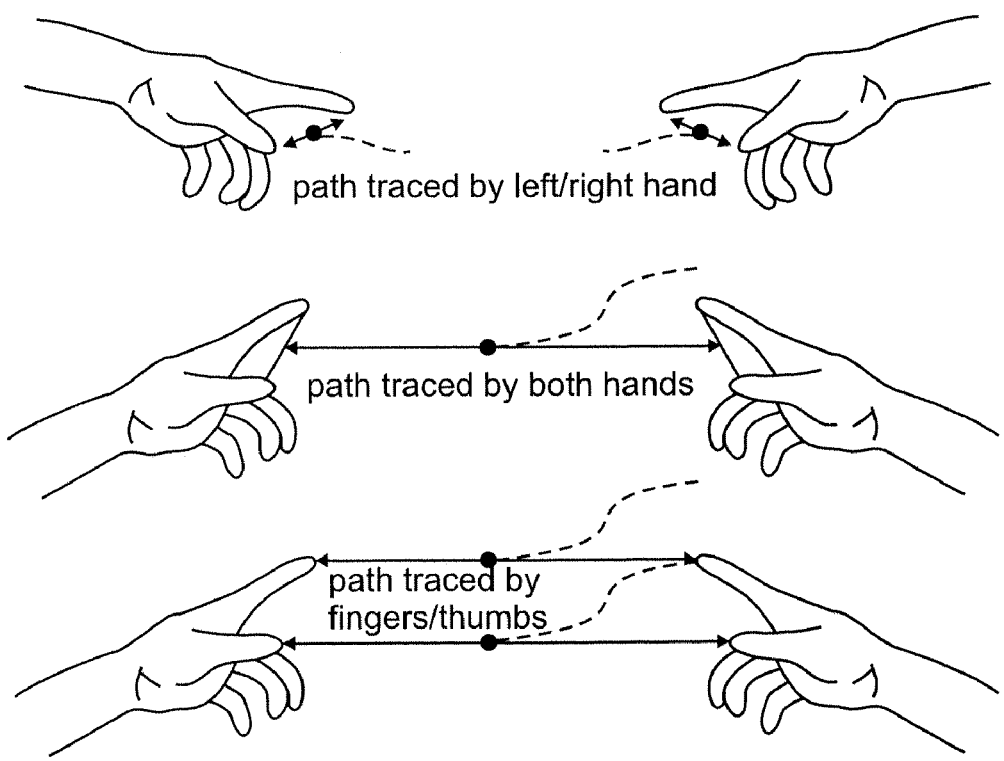
FIG. 18 illustrates the path traced by left/right hand, the path traced by both hands (e.g., using the midpoint between the thumb and fingers), and the path traced by fingers/thumbs in accordance with one or more embodiments of the invention.

FIGS. 17 and 18 illustrate the path traced by an individual finger and the path traced using finger combinations, respectively, in accordance with one or more embodiments of the invention. As illustrated, FIG. 17 shows the path traced by a single fingertip. FIG. 18 illustrates that path traced by left/right hand, the path traced by both hands (e.g., using the midpoint between the thumb and fingers), and the path traced by fingers/thumbs.

The resulting traced surface may be plotted on a coordinate system. The user may have the option of continuously plotting the points, connected by lines using particularly selected sensors. The user may also have the option of selecting the desired measurement (e.g., length, surface area, or volume). Such a length measurement refers to the total, summed lengths of all of the line segments comprising the path that was traced out. The surface area and volume refer to the surface area and volume calculation of the object that was traced out. A Matlab™ script may best fit a 3D mesh to the points to construct the object and calculate the surface area and volume of the shape. Further, the surface area and volume measurement may then be imported and displayed by software of the invention.

In addition, individual points may also be plotted based on the particular sensors selected by the user (e.g., right finger, right thumb, left finger, left thumb). The points may then be saved (e.g., into a spreadsheet or other type of file). The distance from the finger sensors to the origin of a transmitter may also be calculated and displayed.

Localization/Tracking

Embodiments may also allow the user to define the shape of a rigid object in space by representative, reproducible and palpable landmarks for the purpose of localizing its position and orientation. For rigid structures easily characterized by ordinary geometry, such as a cube, the choice of landmarks may be straightforward such as three vertices. For irregular objects, such as a human bone, the choice of landmarks must be more deliberate, both in terms of reproducibility and adequately defining the three dimensional shape of the object. For some objects, enough of the landmarks may be palpable by one hand to define the object and localize it in space. There are consistent postures in which the thumb and fingers work together (pinching, chuck grip, etc.) that can accommodate small objects, depending on the size of the user's hand. For other larger objects, the FT may serve as a probe in order to mark out sufficient points in space to recreate a digital representation of the structure. This use relates back to the procedures of tracing and contour definition described above. Other large objects may be represented by one or more fingers from both hands.

Once an object has been localized, it may be desirable to track any change in the object's position and orientation. The procedure for tracking an object may vary depending on the degrees of freedom with which the object can move and how much position information is desired. There may be limitations with object tracking. For example, object tracking may be limited to rigid objects with palpable landmarks. To track objects with three or more degrees of freedom, at least three instrumented fingers from one or both hands must be able to reach at least three palpable landmarks. Even then, only changes of position within the user's reach are accessible with this approach.

Despite the above-described limitations, there are numerous situations for which this technology would be useful. Take as an example, the Lachman test of the knee, an orthopaedic examination to determine the laxity of knee ligaments. In this test, the examiner firmly grips the femur just above the knee with one hand and the tibia just below the knee with the other. The examiner pulls the tibia forward while stabilizing the femur aiming to assess the amount of translation across the knee. An instrumented version of this test, the KT-1000™, has not only been developed but has become an accepted part of orthopaedic practice. Unlike the present invention, instead of using an examiner's fingertips, the KT-1000™ instrument utilizes affirm mounts and straps, with the goal of delivering a numerical quantity (in millimeters) for the amount of translation. In a similar manner, determining the angular changes between two segments connected at a joint also has tremendous application as will be developed below.

Before describing other uses, the issue of tracking objects with multiple degrees of freedom needs further discussion. It may not always be practical or possible to access three palpable landmarks at the same time, especially with one hand. In these instances, the user may develop strategies for controlling some of the degrees of freedom either in the method of examination or using powers of observation to account for them. As this is intended as an interactive technology, used by a skilled examiner relying on innate discriminative abilities, one or two points on an object may be sufficient to follow certain motions even when the rules of geometry may suggest otherwise.

To properly track the angular change in motion between two or more rigid objects, the user may need to define the axes of rotation and center of rotation. The change between two positions of an object with three or less degrees of freedom can be represented by a point or axis about which the object is rotating. This point (or center) or axis can then be determined by known calculations and the amount and direction of rotation are also then accessible.

To the extent that the object has landmarks accessible to one hand, the angular changes in position can be easily followed in real time. Similarly, if there are two linked objects with accessible landmarks, the angular changes between them are readily determined. The range of motion examination in orthopaedics is a prime example of such an exercise. The examiner usually stabilizes one skeletal segment with one hand while moving another connected at the joint between them to measure the angular range of motion at the joint.

Fracture Reduction

Figure 5:
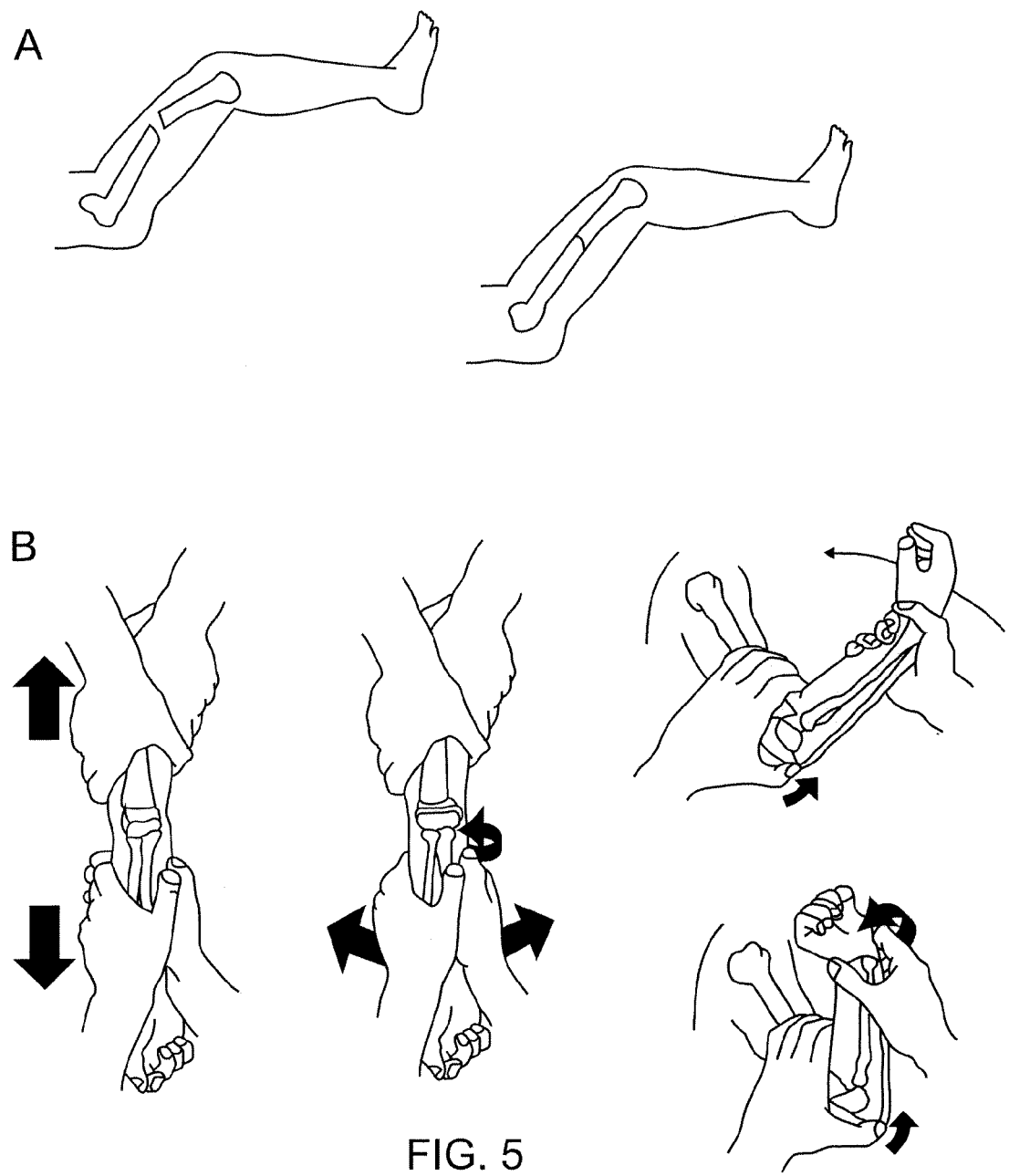
FIG. 5 illustrates the manipulation of broken bones.

Another application that could benefit from the fingertip tracking capabilities of the invention is that of orthopaedics. As described above, accurate skeletal information is useful (if not crucial) for computer-assisted reduction of fractured bones. The clinical practice of fracture reduction involves the identification of a fracture by X-ray, then the application of reduction principles, some form of fixation to the aligned skeletal segment and finally post-reduction X-rays to confirm fracture reduction. As illustrated in FIG. 5, the principles of fracture reduction consistently recommend longitudinal traction of the fractured segment while applying corrective forces to recreate the normal alignment of the segment.

The normal alignment of the segment is estimated by the clinician, in part by his or her knowledge of anatomy, and to a much greater extent by comparison to the patient's unaffected, opposite side. For some applications, this reduction process is performed under fluoroscopy. For many types of fractures, the entire reduction process could be performed without X-ray, guided by information determined by one or more gloves or fingertip-less devices of the invention.

By determining the normal skeletal dimensions of the corresponding uninvolved segment on the other side, the mirror image of this data establishes target parameters for the fractured segment. Using palpable skeletal landmarks on either side of the fracture, the clinician can align the fractured skeletal segment according to these parameters.

Figure 1:
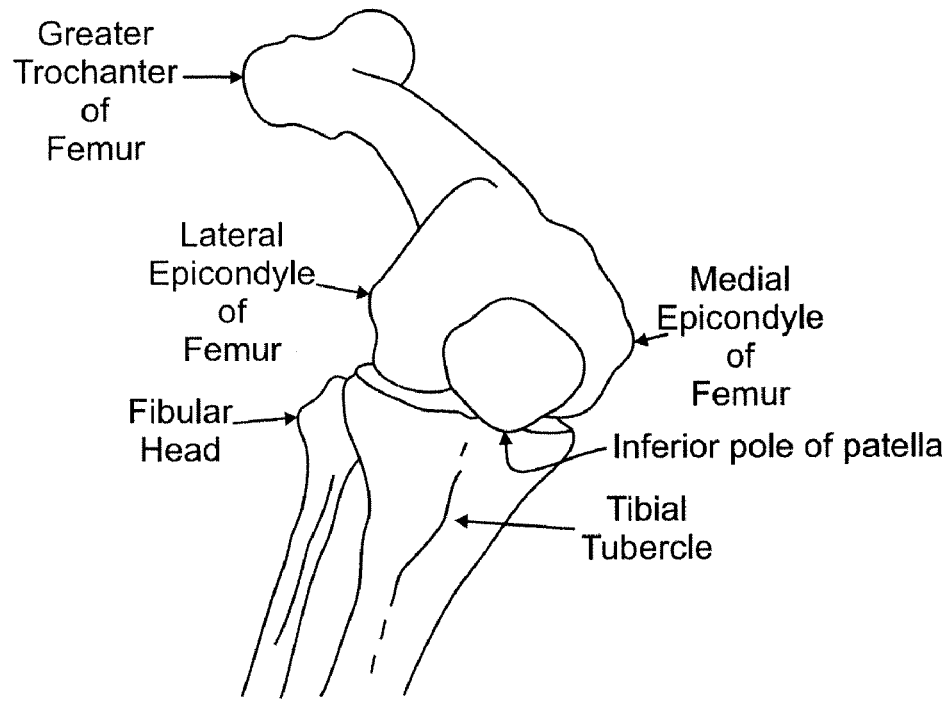
FIG. 1 illustrates the prominent bony landmarks around the knee and up to the hip.
Figure 2:
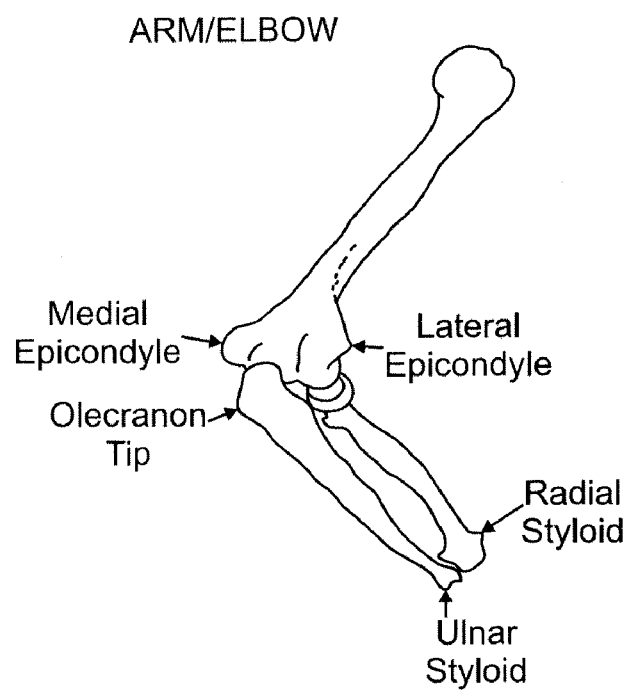
FIG. 2 illustrates the prominent bony landmarks around the elbow.
Figure 3:
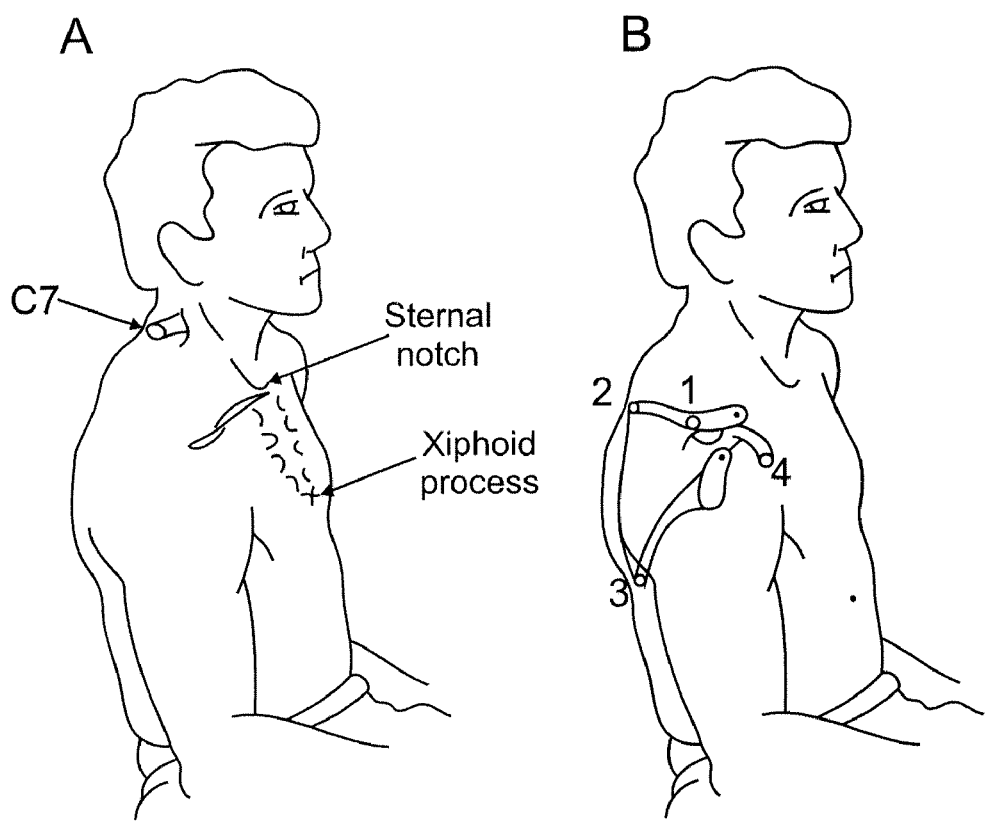
FIG. 3 illustrates the prominent landmarks of the thorax and scapula.

Thus, in orthopedics, the ability to palpate recognizable points of the human skeleton is an essential and necessary skill in diagnosis and treatment. This skill is learned from anatomic study and experience, much guided by learned teachers. Any given bone of the skeleton has consistent areas that protrude sufficiently to aid the examiner in localizing the bone in order frame the rest of the examination. For example, the medial and lateral epincondyles of the knee, along with the perimeter of the patella and the tibial tubercle create a framework from which the examiner can palpate adjacent ligamentous structures such as the medial collateral ligament and the knee menisci (see FIG. 1). The medial and lateral epicondyles of the elbow, and radial and ulnar styloids of the forearm are prominent points that define the arm (see FIG. 2). In the shoulder, the posterior corner of the acromion, the coracoid, the inferior angle and the scapular spine can easily be accessed to generate a representation of this bone (see FIG. 3).

The cluster of points that represent a given bone is informative in its own right but can also form a foundation that can be used in a variety of ways. On its own, this information provides a three dimensional representation of size and proportion of each skeletal segment. Taken together, data of multiple bones begins to define the size and proportion characteristics that distinguish one individual from another. Precise information of these individual differences has great application to many fields and is largely inaccessible in other ways with the exception of radiography. This information has import not only to clinical medicine, but also to fields as disparate as clothes manufacturing and game development using motion capture technology.

In view of the above, the first step for performing a reduction of a fracture is to obtain various points of reference that will assist the examiner in performing the reduction. The invention provides the ability to localize the skeletal segments non-invasively and/or without the use of ionizing radiation. In this regard, the invention offers a means of coordinating bone localization with other skin and surface markers, the use of which are presently encumbered by motion artifacts.

Figure 19:
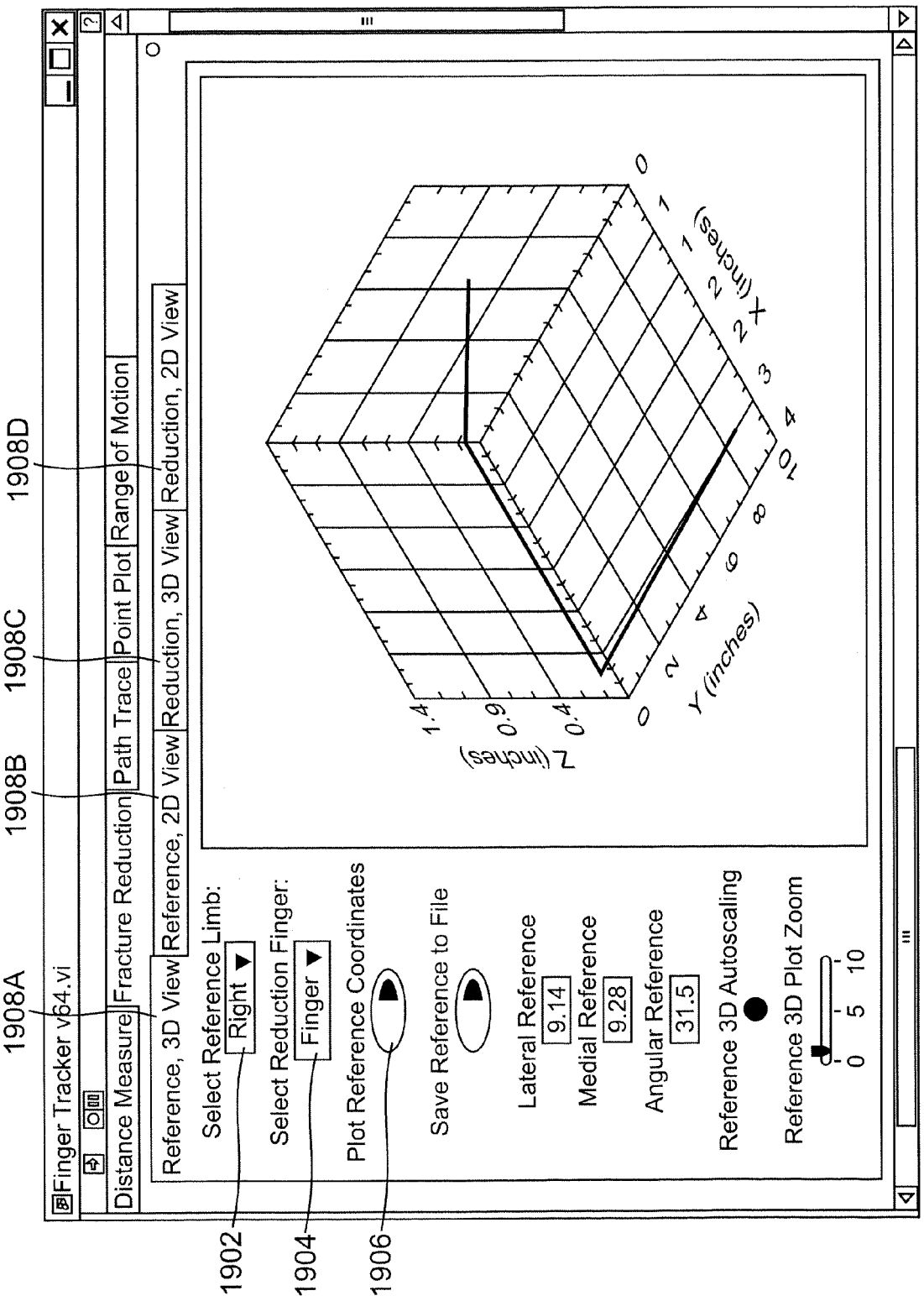
FIG. 19 illustrates a 3D view of a reference plot used in anticipation of a fracture reduction in accordance with one or more embodiments of the invention.

FIG. 19 illustrates a 3D view of a reference plot used in anticipation of a fracture reduction in accordance with one or more embodiments of the invention. As illustrated, the user may first select a reference limb (right or left) 1902. The right and left reference limbs refer to the limb that is serving as a reference to the broken bone. For a right limb, the left hand will act as the stationary pivot, and for a left limb, the right hand will act as the pivot. For example, for a patient's right elbow, the left hand will be holding onto the elbow at the epicondyles, while the right hand will be holding onto the wrist at the styloids. Also, the fingers will always be holding onto the medial side of the limb, while the thumbs will always be holding onto the lateral side.

The select reduction finger drop down button (finger or thumb) 1904 refers to the finger for which the reduction is taking place, with the opposite finger acting as the stationary pivot. For example, for a patient's right elbow using the finger case, the right finger will be holding onto the radial styloid and reducing it, while the right thumb will be holding onto the ulnar styloid (see FIG. 2).

The plot reference coordinates 1906 button plots the four prominences of the forearm: the lateral and medial epicondyles, and the radial and ulnar styloids. The lateral side is connected by a solid line, i.e. between the lateral epicondyle and the radial styloid, while the medial side is connected by a dotted line, i.e. between the medial epicondyle and the ulnar styloid. In addition, the user may save the plotted reference to a file (e.g., as a spreadsheet or otherwise), display the reference distance (lateral or medial) between points (e.g., between the lateral/medial epicondyle and the radial/ulnar styloid on the lateral/medial size), display a reference angle (e.g., between a frontal side vector pointing from the ulnar styloid to the radial styloid, and the proximal side vector pointing from the medial epicondyle to the lateral epicondyle), toggle autoscaling for the fracture reference plot, and/or adjust the (x,y,z) scales of the fracture reference plot.

As illustrated in FIG. 19, various tabs 1908A-1908D may provide different views for the user to interact with. For example, rather than displaying the 3D plot in tab 1908A, the user can opt to display a 2D view of the fracture reference using tab 1908B. In such a 2D view, a top view, axial view, and/or side view of the 2D plot of the fracture reference may be displayed.

Figure 20:
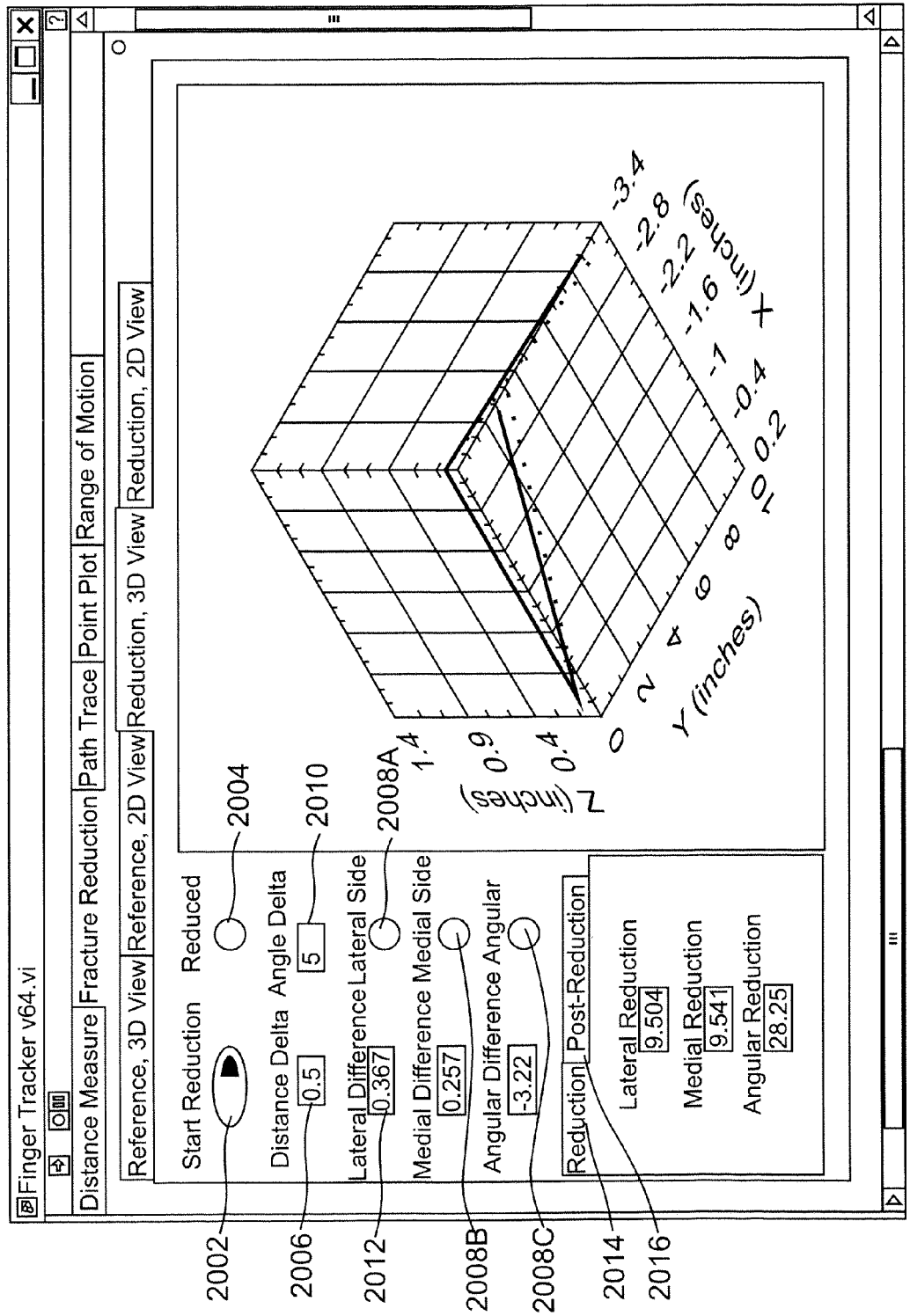
FIG. 20 illustrates a 3D view of a fracture reduction display in accordance with one or more embodiments of the invention.

Once the fracture reference has been determined, the fracture reduction procedure may be performed. FIG. 20 illustrates a 3D view of a fracture reduction display in accordance with one or more embodiments of the invention. The start reduction button 2002 starts the fracture reduction procedure. The reduced radio button 2004 will be active/on once the fracture has been fully reduced. The distance delta field 2006 displays the threshold for the lateral and medial reduction distances relative to the reference distances. Once the reduction distance comes within this threshold of the reference distance, the appropriate LED 2008A-2008B lights up indicating the side that has been successfully reduced. The angle delta 210 displays the threshold for the reduction angle relative to the reference angle. Once the reduction angle comes within this threshold of the reference angle, an "Angular" LED 2008C lights up indicating that the angle has been successfully reduced.

The lateral difference field 2012 displays the difference between the reduction distance from the lateral epicondyle to the radial styloid and the reference distance. This value is positive when the reduction distance is greater than the reference distance, and negative when the reduction distance is less than the reference distance. The lateral slide LED 2008B turns on when the lateral side of the fracture has been reduced. The medial difference field displays the difference between the reduction distance from the medial epicondyle to the ulnar styloid and the reference distance. This value is positive when the reduction distance is greater than the reference distance, and negative when the reduction distance is less than the reference distance. Similarly, the angular difference field displays the difference between the reduction angle between the frontal and proximal side vectors and the reference angle. This value is positive when the reduction angle is greater than the reference angle, and negative when the reduction angle is less than the reference angle.

There are two mini-tabs 2014 and 2016 within the fracture reduction view that provide more detailed information. The reduction tab 2014 displays the lateral reduction, medial reduction, and angular reduction (i.e., the reduction distances and angle relevant to the fracture being reduced). The post-reduction tab 2016 provides the ability for the user to save the array of fracture reduction points to a file (e.g., as a spreadsheet or otherwise), to autoscale the reduction plot, and/or to adjust the (x,y,z) scales of the fracture reference plot.

Figure 21:
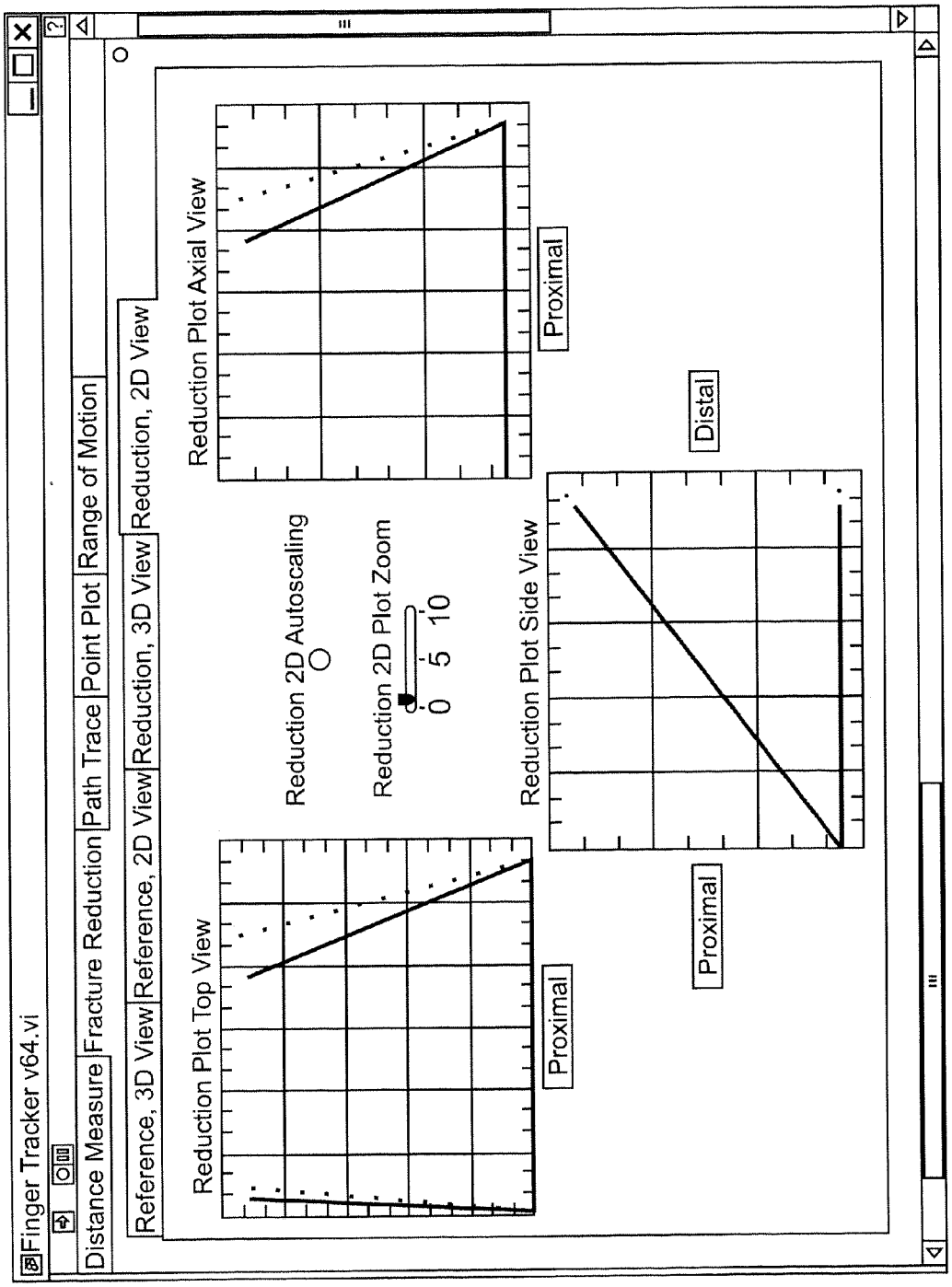
FIG. 21 illustrates a 2D view of a fracture reduction plot in accordance with one or more embodiments of the invention.

Similar to the fracture reference, the user may also opt to display a 2D view 1908D of the various fracture reduction plots in accordance with one or more embodiments of the invention. Such 2D plots may show a top view, axial view, and side view of the fracture reductions. Certain vectors may always be displayed in certain locations (that may be user specified). FIG. 21 illustrates such a 2D view in accordance with one or more embodiments of the invention. The various text boxes adjacent to the plots illustrate which side the particular vectors are always displayed in (e.g., bottom/left for proximal vector or right for distal vector).

Thus, the above description illustrates a specific example of the various display screens and process for performing a fracture reduction in accordance with the invention.

In addition to assisting the surgeon in localization of surgical anatomy as described above with the description of augmented reality goggles or fracture reference, computer-assisted surgeries may also benefit from the invention. For example, joint replacements such as knee and hip replacements [31] may benefit from the invention. Such technologies/surgeries may use navigation system guided techniques to improve on the surgical placement of joint prostheses and resultant alignment of the limb. To accomplish this, an important part of the technique involves sampling local and distant anatomy usually with the use of a pointer and an optical tracking unit. Accordingly, such a procedure could be greatly facilitated by use of fingertip tracking technology (of the invention) to define these anatomic landmarks and the surgical procedure.

Range of Motion

Figure 4:
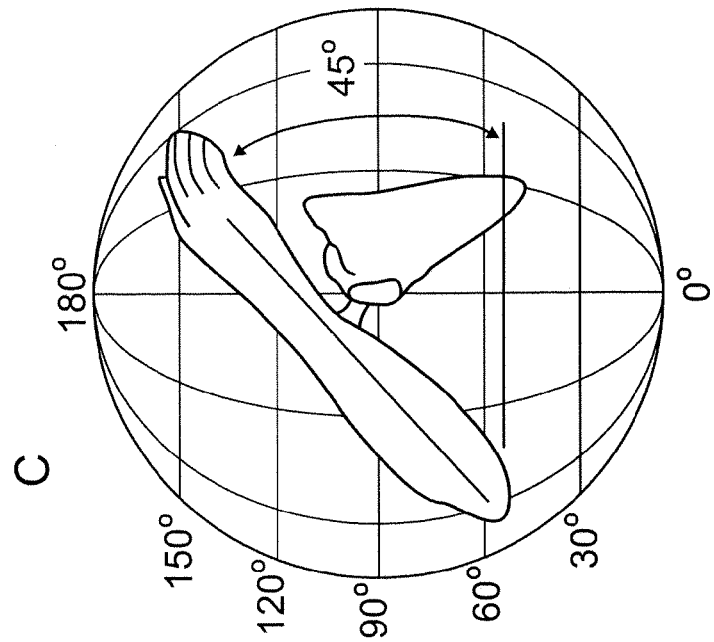
FIG. 4 illustrates skeletal landmarks used to construct a local coordinate system to define the range of motion between the scapula and humerus with precision.
Figure 4:
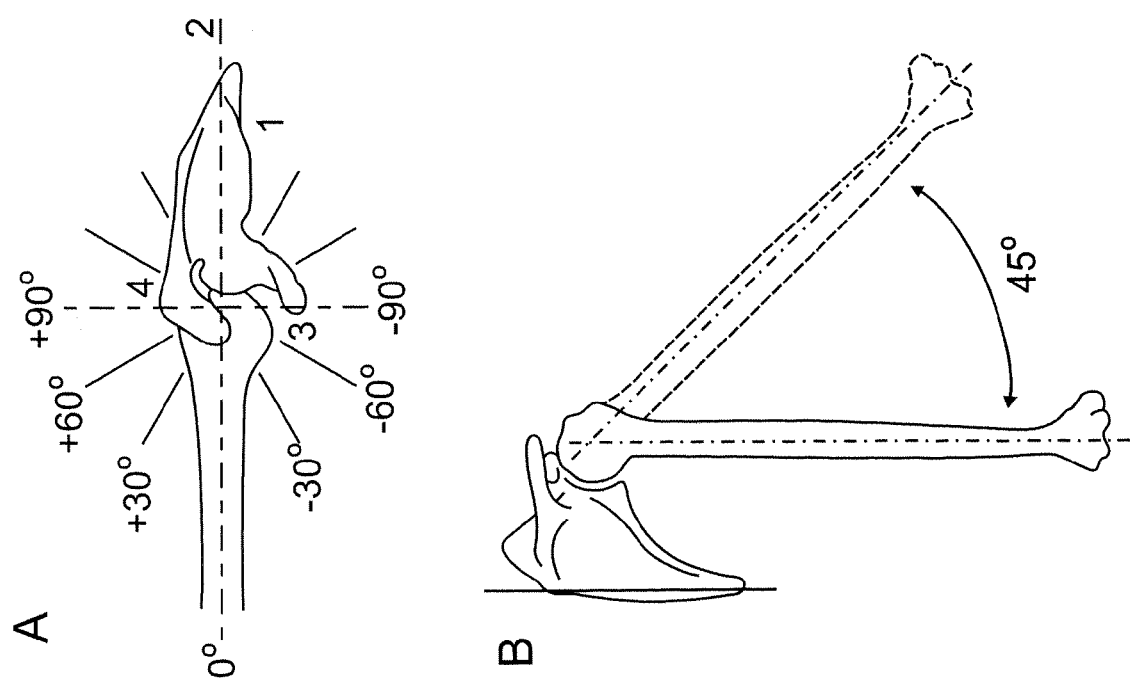

Having an accurate representation of the skeleton provides the basis for another application of the present invention—defining the relative motion between any adjacent skeletal segments (see FIG. 4). If two segments are connected, the range of motion (ROM) so measured defines the range of motion of the interposed joint.

Measuring joint ROM is an integral part of clinical orthopedics. It is a standard part of nearly every orthopedic exam. Typically, the examiner moves a joint through its range of motion and makes a visual estimate of the angular changes observed. As described above, for more precise measurements, it is customary to lay a transparent goniometer next to the joint to determine this angle. However, such prior art methodologies have problems with respect to accuracy and known intra and inter observer variability.

In accordance with one or more embodiments of the invention, an examiner instrumented with at least two fingertip trackers on each hand may palpate defined points of two adjacent skeletal segments, and thereby measure the angular changes between the skeletal segments with exceptional precision. Further, the use of the fingertip tracking device of the invention enables a convenient method of recording the data.

Figure 22:
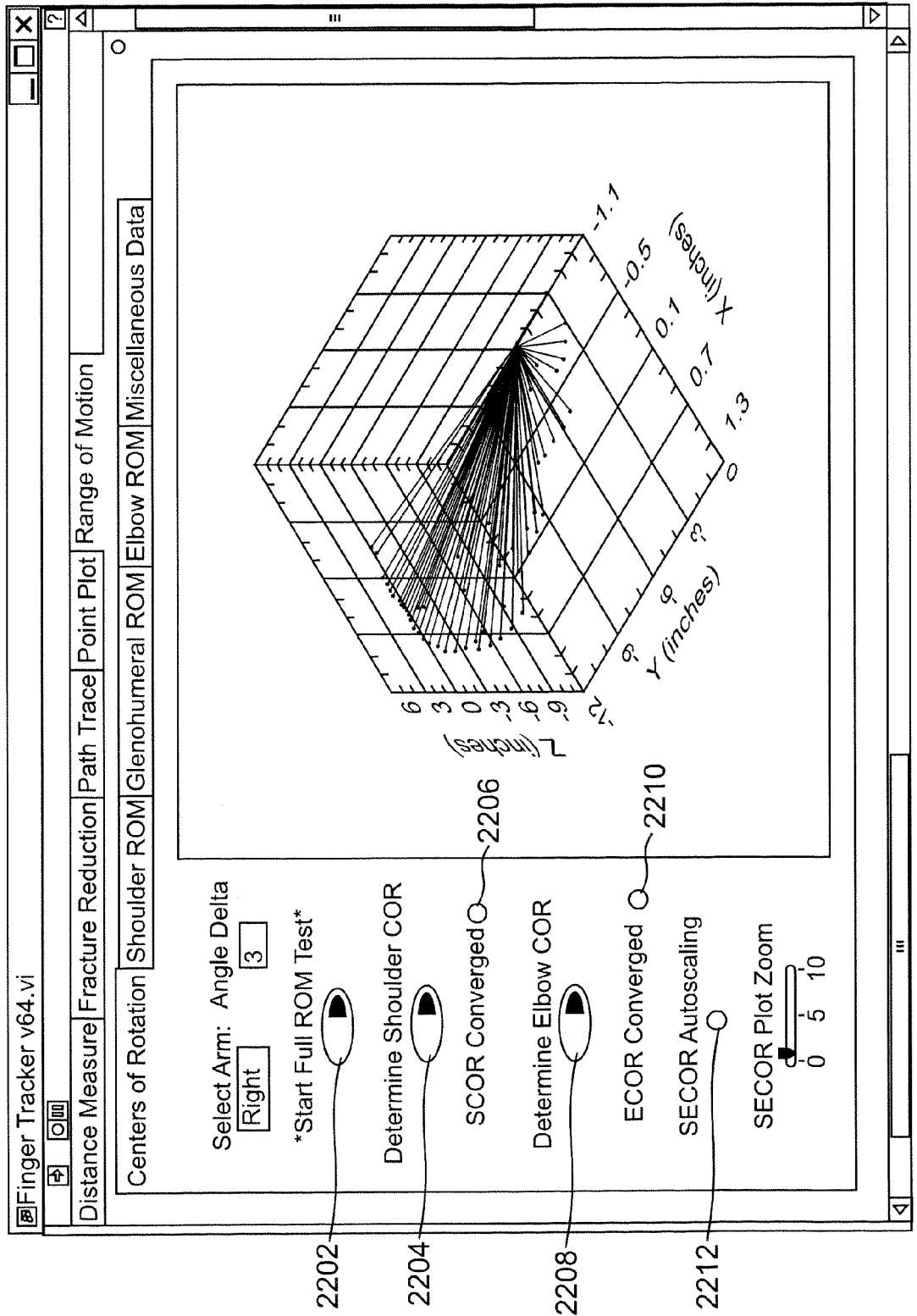
FIG. 22 illustrates a center of rotation display used in range of motion examinations in accordance with one or more embodiments of the invention.

The various range of motion determinations may be plotted for better use and analysis. FIG. 22 illustrates a center of rotation display used in range of motion examinations in accordance with one or more embodiments of the invention. As illustrated, the user can select the left arm and/or right arm to identify the patient's arm to be examined, each of which specifies a standard choreography for the examiner. The angle delta specifies the tolerance, in degrees, by which angles to axes/planes are measured. For example, in a shoulder external rotation test, the humeral axis must be positioned parallel to the sternal axis. Thus, an angle delta of 3 corresponds to an acceptable range of $-3°$ to $+3°$ for the angle between the humeral and sternal axis for them to be considered parallel.

Once the appropriate arm and angle delta have been selected, the user may click the Start Full ROM Test button 2202. The activation of the button starts the complete ROM series of tests (e.g., in the following order): Determine Shoulder COR, Determine Elbow COR, navigate to Shoulder ROM Tab, Determine Thoracic Plane, Measure External Rotation, Measure Elevation, navigate to Glenohumeral ROM Tab, Determine Scapular Plane, Measure External Rotation, Measure Internal Rotation, navigate to Elbow ROM Tab, Measure Extension, Measure Flexion, Measure Pronation, and Measure Supination.

As the user proceeds through the ROM examination, various points and data are plotted on the display.

The first step is determining the shoulder center of rotation (COR) referring to the point about which the upper arm rotates in the glenohumeral joint. The user may click the Determine Shoulder COR button 2204 once to continuously plot the sweep of vectors pointing from the midpoint of the posterior corner of the acromion and the coracoid to the midpoint of the lateral and medial epicondyles. The button 2204 may be clicked again to stop the data collection and automatically calculate the shoulder center of rotation. A Matlab™ script may be used to best-fit a sphere to the array of vectors from the test. The calculated center and radius of the sphere (corresponding to the center of rotation of the shoulder and the length of the upper arm) may then be imported and displayed (i.e., from Matlab™) using software of the invention. If the Matlab™ algorithm for calculating the shoulder center of rotation converges, the LED light 2206 will activate.

The next step is that of determining the elbow center of rotation. The user may click the button 2208 once to continuously plot the sweep of vectors pointing from the midpoint of the lateral and medial epicondyles to the ulnar styloid. The button 2208 may be clicked again to stop the data collection and automatically calculate the elbow center of rotation. A Matlab™ script may best-fit a circle in 3D to the array of vectors from the test, and software of the invention may import and display the calculated center, normal to the plane, and radius of the circle, corresponding to the center and axis of rotation of the elbow, and length of the forearm. The elbow center of rotation converged LED 2210 activates if the Matlab™ algorithm for calculating the elbow center of rotation converged. The user may also opt to autoscale the plot using the autoscale button 2212.

Figure 23:
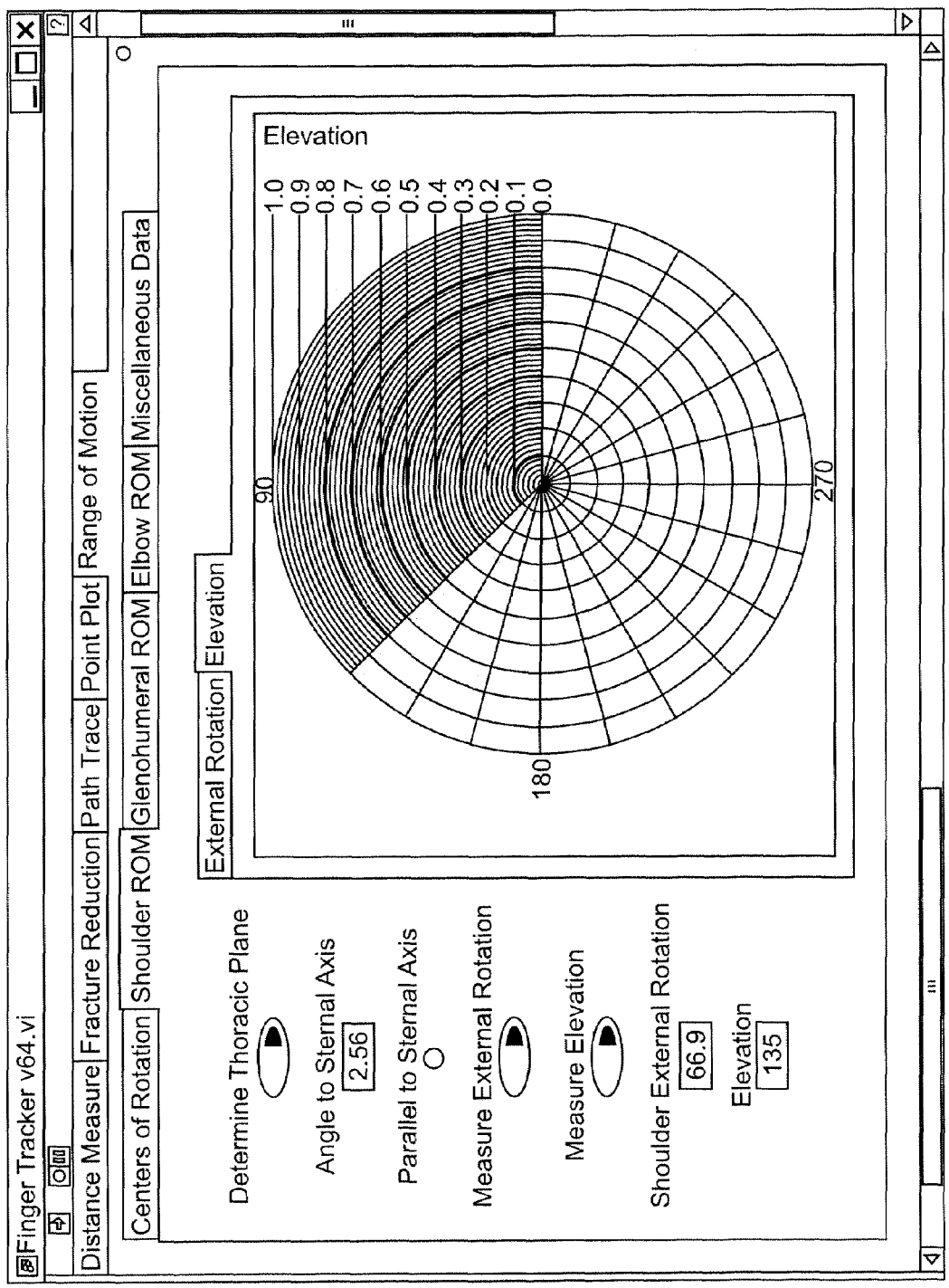
FIG. 23 illustrates an elevation tab plotting the shoulder range of motion in accordance with one or more embodiments of the invention.

Once the center of rotation has been determined, the shoulder range of motion may be evaluated. FIG. 23 illustrates an elevation tab plotting the shoulder range of motion in accordance with one or more embodiments of the invention. The user first determines the thoracic plane. For a patient's right arm, the examiner touches the C7 process with his left finger and the sternal notch with his right finger, and then the xyphloid notch with his right finger. For a left arm, the examiner touches the C7 process with his right finger and the sternal notch with his left finger, and then the xyphloid notch with his left finger. The thoracic plane is formed from these three points. The normal to the plane points from the thorax towards the shoulder, and the sternal axis points from the sternal notch to the xyphloid notch.

The system may also display the angle that the humeral axis makes with the sternal axis referred to as the Angle to Sternal Axis. In addition, an LED may activate if the humeral axis is parallel to the sternal axis. The user may then elect to measure the external rotation. For a patient's right arm, the examiner first holds the shoulder with his left hand and the elbow with his right hand and positions the humeral axis parallel to the sternal axis. The examiner then moves his left hand to the elbow and his right finger to the ulnar styloid, and rotates the forearm into full external rotation. For a patient's left arm, the examiner first holds the shoulder with his right hand and the elbow with his left hand and positions the humeral axis parallel to the sternal axis. The examiner then moves his right hand to the elbow and his left finger to the ulnar styloid, and rotates the forearm into full external rotation.

The elevation may also be measured. For a patient's right arm, the examiner holds the shoulder with his left hand and the elbow with his right hand, and rotates the upper arm into maximum elevation without inducing body movement. For a patient's left arm, the examiner holds the shoulder with his right hand and the elbow with his left hand, and rotates the upper arm into maximum elevation without inducing body movement.

The invention may display the external rotation and elevation of the shoulder.

Similar to the shoulder ROM, the invention may also provide the ability to measure the glenohumeral ROM and elbow ROM. For each measurement, a specific sequence/protocol may be required to be followed to accommodate the calculations performed by the software. Further, various tabs may allow the user to view data and plots of the information being measured/obtained. For example, for elbow ROM measurements, flexion/extension and pronation/supination tabs may display plots of the respective information.

The following describes a general protocol intended for a single examiner, using four sensors (two on each hand) to measure three elements of range of motion: (1) the glenohumeral rotational arc at 45° humero-scapular elevation; (2) elbow flexion and extension; and (3) forearm pronation and supination. However, conventional measures of shoulder range of motion (elevation, external/internal rotation) may not be included in the protocol but could be included in accordance with alternative embodiments.

The first ROM measurement is that of glenohumeral rotational arc at 45° humero-scapular elevation. This measures the range of external and internal rotation with the humerus elevated 45° in the scapular plane. 0° is arbitrarily defined as the position in which the forearm (elbow flexed to 90°) is perpendicular to the scapular plane. The examiner first places one hand (e.g., one fingertip on the coracoid and the other on the posterior acromion) and the other hand at the elbow (e.g., one fingertip on the medial epicondyle and the other on the lateral), moves the humerus through a ROM and establishes the center of rotation.

The hand at the elbow is then repositioned to use the two instrumented fingertips to localize two additional scapular landmarks—the medial border of the scapular at the intersection of the scapular spine and the inferior angle of the scapula. These two points then define a zero position for humeral elevation relative to the scapula. The scapular plane is also defined by these two points and a third point, the mid-point between the coracoid and the posterior acromion. The second hand is returned to the elbow (epicondyles) and the humeral axis is positioned at 45° elevation in the scapular plane.

The arm is rotated to its end range in external rotation. The axis of the ulna is defined (olecranon tip to ulnar styloid), the angle of external rotation is measured. The arm is rotated to the end range of internal rotation and this position is measured. Note that the ulnar axis could have already been defined relative to the epicondylar axis and this would save a step.

The second measurement is that of elbow flexion and extension. 0° is defined by the parallel position of the ulnar axis and humeral axis. The elbow is taken through a range of motion sufficient to establish the trochlear axis. The arm is positioned at the end range of extension and a measurement is taken. The arm is then positioned at the end range in flexion and another measurement is taken.

The third measurement is that of forearm pronation and supination. 0° is defined by the parallel alignment of the radial and ulnar styloids and the plane of the arm (humeral and ulnar axes in 90° elbow flexion). The forearm is rotated to full supination. The position of the radial and ulnar styoids are then assessed. The same procedure may be followed for pronation.

Figure 24:
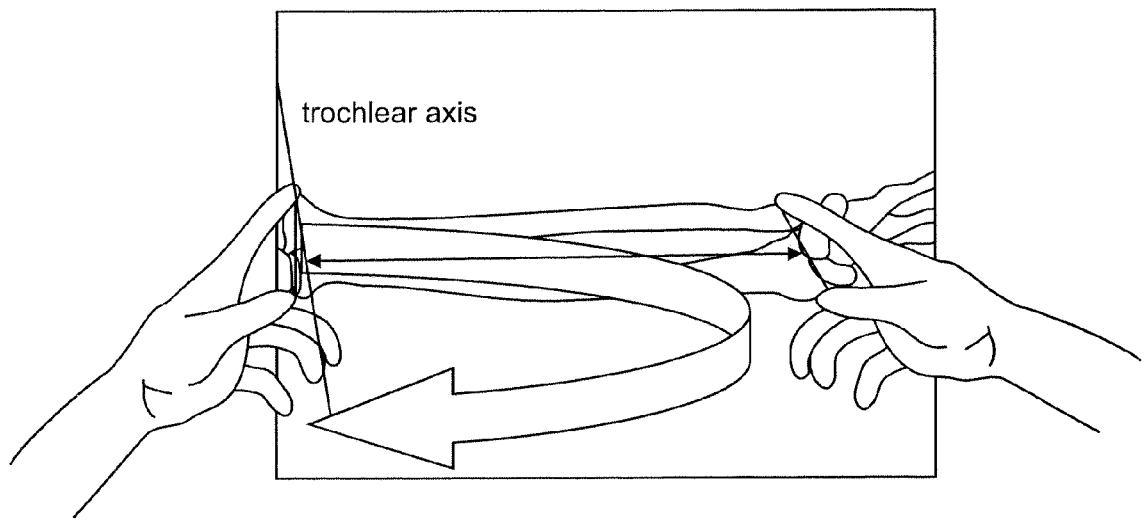
FIGS. 24 and 25 illustrate an elbow flexion/extension test and elbow pronation/supination test illustrating the fingertips (with sensors—not displayed) respectively in accordance with one or more embodiments of the invention.
Figure 25:
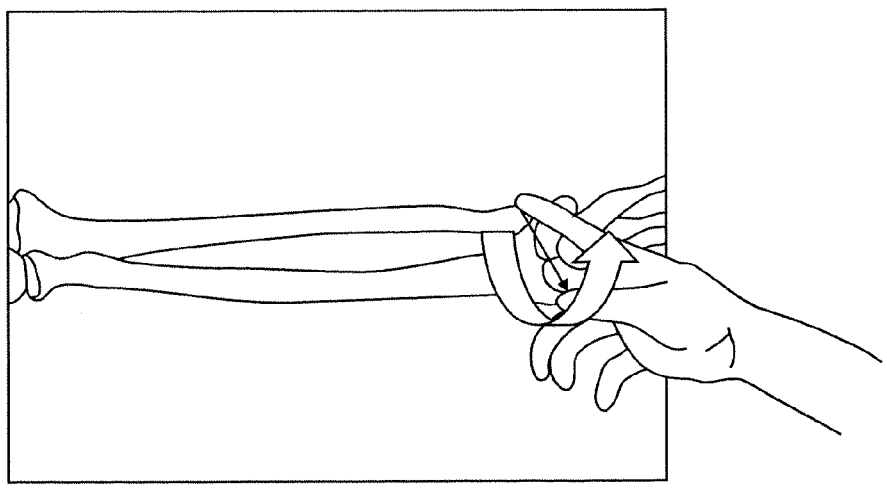

As described above, all of the measurements are obtained through the sensors attached to the fingertips of the examiner during the ROM examination. For example, to measure the extension during an elbow ROM examination, the examiner holds the elbow with his left hand and the ulnar styloid with his right finger, and rotates it into full extension. For a patient's left arm, the examiner holds the elbow with his right hand and the ulnar styloid with his left finger, and rotates it into full extension. FIGS. 24 and 25 illustrate an elbow flexion/extension test and elbow pronation/supination test illustrating the fingertips (with sensors—not displayed) respectively.

Figure 26:
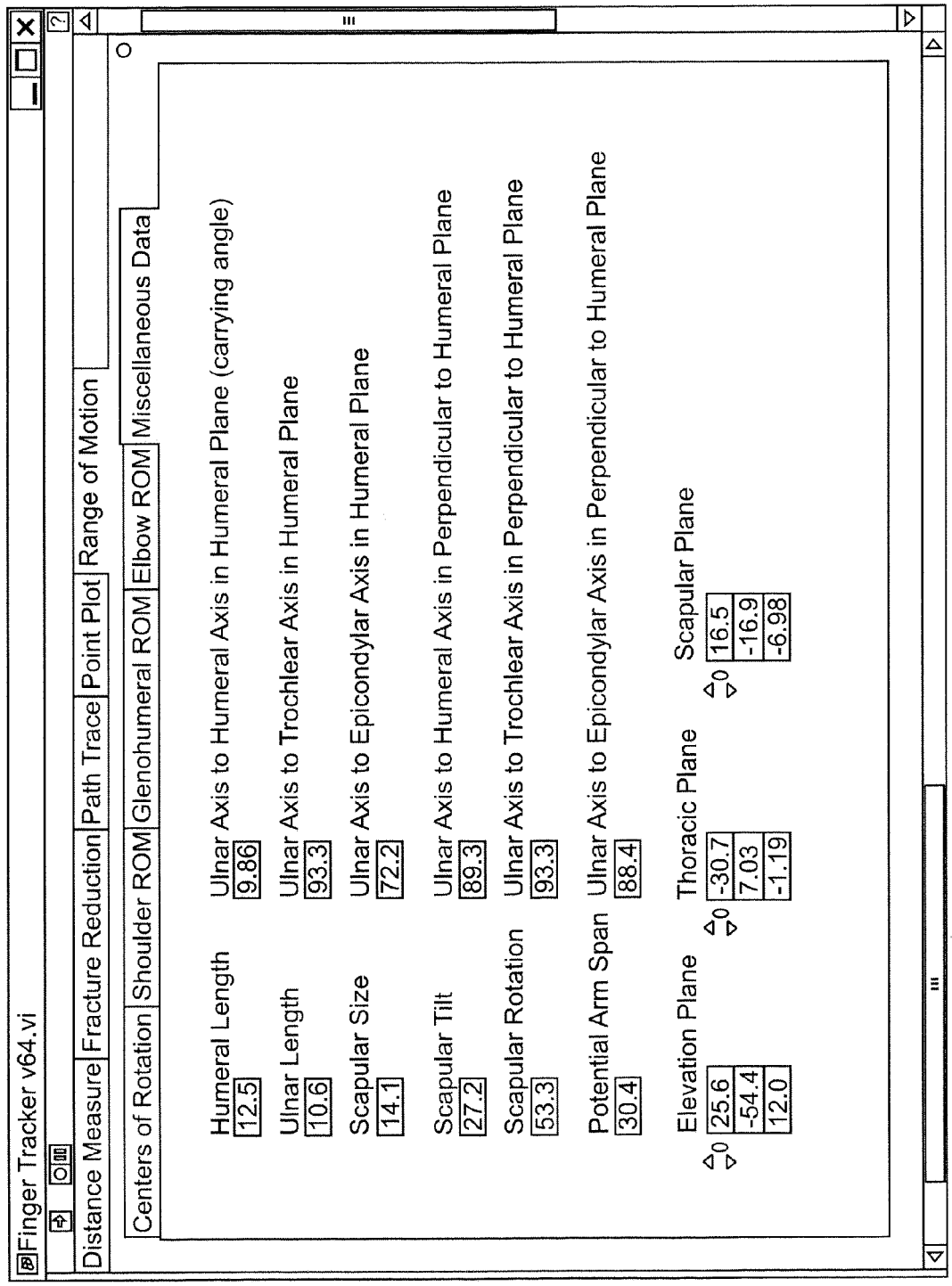
FIG. 26 illustrates the various miscellaneous data that may be calculated and displayed in accordance with one or more embodiments of the invention.

In addition to the specific information displayed for the different range of motion examinations, miscellaneous data that may be useful to the examiner may also be displayed. FIG. 26 illustrates the various miscellaneous data that may be calculated and displayed in accordance with one or more embodiments of the invention. As illustrated, the following information may be calculated and displayed:

Humeral Length—Displays the length of the upper arm.
Ulnar Length—Displays the length of the forearm.
Scapular Size—Displays the size of the scapula, calculated as the area of the triangle formed by the top and bottom processes of the scapula and the midpoint of the posterior corner of the acromion and the coracoid.

Scapular Tilt—Displays the angle between the scapular axis and the sternal axis.

Scapular Rotation—Displays the angle between the axis from the top process of the scapula to the shoulder center of rotation and the normal to the thoracic plane.

Potential Arm Span—Displays the summed length from the thoracic plane to the shoulder center of rotation, the humeral length, and the ulnar length, multiplied by two.

Ulnar Axis to Humeral Axis in Humeral Plane (carrying angle)—Displays the angle between the humeral axis and the rotation of the ulnar axis onto the humeral plane.

Ulnar Axis to Trochlear Axis in Humeral Plane—Displays the angle between the trochlear axis and the rotation of the ulnar axis onto the humeral plane.

Ulnar Axis to Epicondylar Axis in Humeral Plane—Displays the angle between the projection of the epicondylar axis onto the humeral plane and the rotation of the ulnar axis onto the humeral plane.

Ulnar Axis to Humeral Axis in Perpendicular to Humeral Plane—Displays the angle between the humeral axis and the rotation of the ulnar axis onto the perpendicular to the humeral plane.

Ulnar Axis to Trochlear Axis in Perpendicular to Humeral Plane—Displays the angle between the trochlear axis and the rotation of the ulnar axis onto the perpendicular to the humeral plane.

Ulnar Axis to Epicondylar Axis in Perpendicular to Humeral Plane—Displays the angle between the projection of the epicondylar axis onto the humeral plane and the rotation of the ulnar axis onto the perpendicular to the humeral plane.

Elevation Plane—Displays the normal to the shoulder elevation plane.

Thoracic Plane—Displays the normal to the thoracic plane.

Scapular Plane—Displays the normal to the scapular plane.

Such miscellaneous information may be useful is evaluating the patient and determining the proper course of treatment.

Probe in Clinical Medicine

While various different types of uses of the invention are described above, further uses are also within the scope of the present invention. Many areas of medicine require measuring the size and depth of physical structures relevant to a patient's examination. Even in dermatology, the size and contour of a lesion are relevant. Using fingertip technology, an examiner could map the exact dimensions of a lesion by tracing it with a fingertip (see the description of tracing above). The same process could be applied to lumps, nodules and masses providing dimensions of height and thickness in a calculation of contour and volume.

Other clinical fields often palpate structures that are beneath the skin to estimate their size and thickness. Many of these are accessible to the examiner's fingertips in the same way. This applies not only to abnormal masses but also to normal structures such as the inferior edge of the liver (distance from lower rib), the ovaries, the prostate, etc. For some of these structures, the prevailing clinical standard is the information gleaned from a "bimanual examination". These examinations require the user to palpate objects between the fingertips of both hands and make an estimate of the objects size and thickness. As such, this data acquisition technology would greatly facilitate these examinations. For example, using the sensors, accurate information may be acquired relating to the size and depth of an object or part of the anatomy.

Interactive Radiology

Embodiments of the invention may also be used in radiology or the area in the medical center that houses large imaging technology. With the increasing availability of various kinds of total body scans, a technology that let the examiner correlate the position of their examining fingertip (e.g., the region or focal point of pain) to a real time anatomical scan would offer a potent diagnostic and interventional tool.

Training in Medicine

In addition to providing consistent objective measurements of the anatomy, embodiments of the invention may also be useful as a training tool. For example, when a student instrumented with fingertip technology uses models, or perhaps cadavers, to learn anatomical and examinational skills, a teacher or perhaps computer can evaluate if the student is palpating the correct structures.

Miscellaneous Medical Uses.

One or more embodiments of the invention can be used in a variety of medical contexts. For example, the thickness of various body parts may be examined. In this regard, a fold of skin may be pinched to determine the thickness of the epidermis in particular locations. Such measurements would provide information relating to an edema and/or the mobility and turgor of the skin. In yet another embodiment, two hands may be used to palpate areas of the body in a particular manner/method. For example, the vaginal wall, cervix, etc. may be palpated to assist in obtaining abnormal/normal findings. Further, the size of the uterus may be determined thereby providing useful information including the existence of cysts or estimating the size of a fetus. Other measurements or palpations would allow one to determine the size of an ovary. In males, palpating in a particular manner could lead to data relating to the prostrate, such as the size of the prostrate and any abnormalities, or the existence of a hernia.

Palpating breasts may lead to a determination of breast mass size, the existence of masses/cysts, a determination of a consistency of a breast lesion or an identification of the size/borders of a breast lesion/mass. Palpating in a particular manner under the arm could also lead to data relating to the lymph nodes.

Palpating the neck in a particular manner could provide relevant thyroid information (e.g., size) while palpating the stomach region could lead to data relating to internal organs such as the size of the kidney or size of aorta.

The above general and specific applications may also be used in veterinary medicine context.

Any tool or device held in a characteristic and reproducible way by the fingers or hand may be conceptualized as extensions of the fingertips, allowing the user exceptionally precise information on the position and orientation of the device as well. To the extent that this data is incorporated into an algorithm aiming to achieve a particular goal, this information can guide the manipulation of the tools. In combination with anatomic information obtained from detailed imaging studies, surgical manipulation of objects could achieve an unprecedented level of precision. Using telemedicine, a more highly skilled surgeon could even remotely guide the hands of a less skilled one. In this regard, the applications in medical education are also significant.

In addition to medical uses, the fingertip tracking device may also be used in a non-medical context. For example, any application, even those outside of clinical medicine, that utilizes accurate skeletal information would benefit from this technology. Additionally, any area of human activity that employs manual dexterity to analyze objects and manipulate them would benefit in the same manner. Potential uses range from all areas of industry that require manual dexterity to improvement of performance in sports.

Logical Flow

Figure 27:
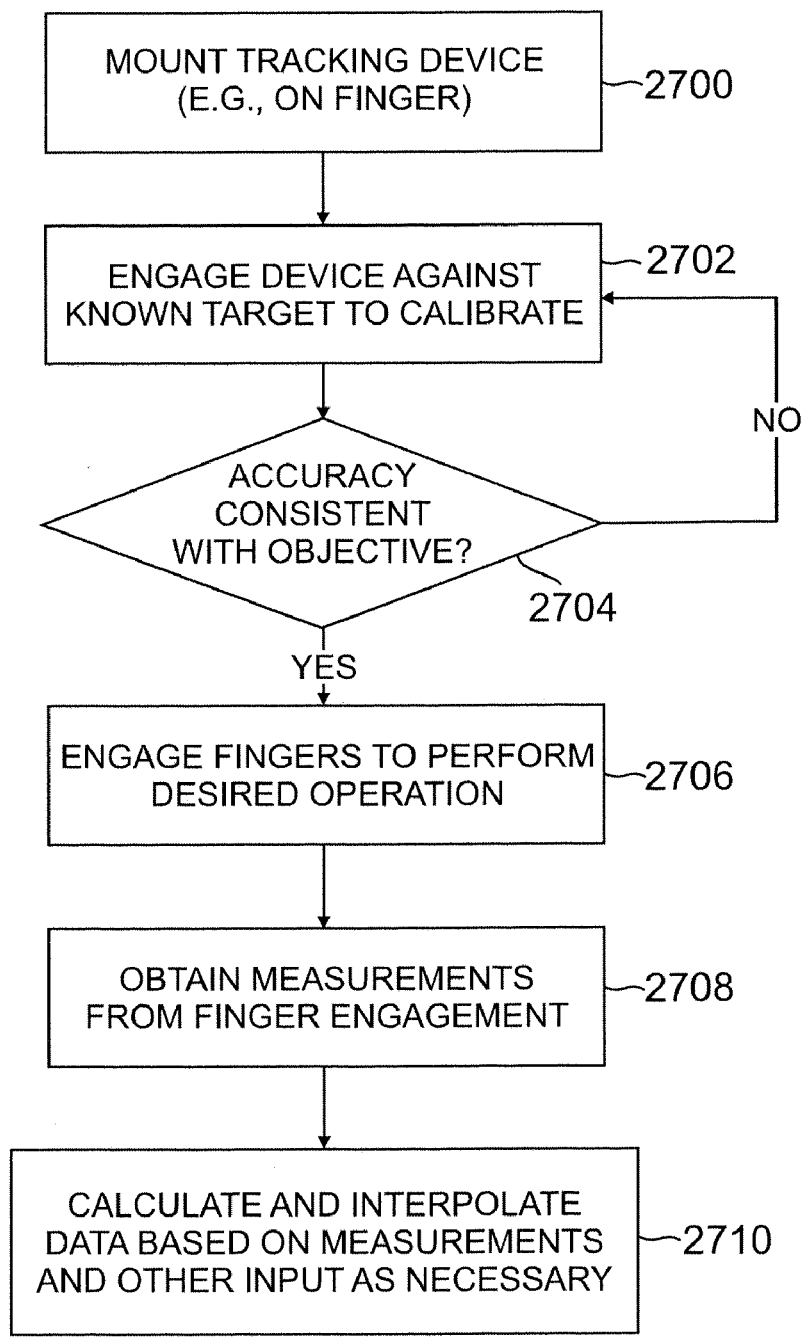
FIG. 27 illustrates the logical flow for using a fingertip tracking in accordance with one or more embodiments of the invention.

FIG. 27 illustrates the logical flow for using a fingertip tracking in accordance with one or more embodiments of the invention. At step 2700 the tracking device (e.g., an electromagnetic motion sensor) is mounted (e.g., on the fingertips as described above). The sensor is communicatively coupled to a computer as illustrated in FIG. 6.

At step 2702, the device is engaged against a known target to calibrate the device with the desired level of accuracy. Such a calibration may also include correcting the data using a best-fit calibration function. Further, the calibration may involve multiple steps. Such steps may include a determination of a known point followed by the calibration of the mounted sensor to the known point. In this regard, the determination of the known point may involve inserting the sensor into a calibration device prior to mounting the sensor on the fingertip. Such a calibration device may comprise one or more known points. The coordinates of the known points are stored based on the sensor to provide one or more locations in space. Once the sensor is mounted, the user touches the one or more known points/locations with the fingertip.

A determination may then be made regarding the accuracy of the user's touch to the known points. Thus, at step 2704 a determination is made regarding whether the level of accuracy is consistent with the desired objective (i.e., if the calibration process is complete or complies with the user's objectives or is within a defined threshold). If the consistency level is below that desired (or outside of the defined threshold), the process repeats with step 2702 for further calibration. The calibration process further provides for subtracting the coordinates of the known points from the coordinates measured by the sensor to provide a vector pointing from the sensor to the known point at the fingertip.

The vector is then used to determine/calculate a matrix/rotation matrix that will rotate the vector to account for a position of the fingertip. In this regard, any actual measurements taken with the fingertips can be adjusted accordingly (based on the calibration).

Once calibration is complete the process continues at step 2706 where the user engages the fingers (i.e., with the fingertip tracking device mounted) to perform the desired operation. As described above, such desired operations may be general or specific in the medical field.

At step 2708, measurements are obtained from the fingertip device engagement of step 2706. In other words, as described above, the amount of movement of the fingertip(s) as calibrated with respect to an established coordinate system is obtained. Such measurements may include a distance between two sensors on a single hand, a distance between a midpoint of two sensors on a right hand to a midpoints of two sensors on a left hand, a distance between a sensor on the left hand and a sensor on a right hand, a depth of an object on the person being examined, etc. In addition, such measurements may be obtained from an area not visible to the examiner (e.g., not directly visible to the human eye) but merely accessible to the fingertips.

The invention then utilizes the measurements to obtain/calculate (and potentially interpolate) data based on measurements and other input at step 2710. Such data may include the plotting of the measurements on a display device of the computer. Further, such other input may comprise an activation button (e.g., a footswitch), visual identifiers, user input into a computer (e.g., via a selected operation that identifies particular measurements that the user identifies are being obtained), or any other input that could be used. In this regard, the computer system may prompt the user to follow an established sequence of events/measurements. At each step, the user can signify the fingertips are in the correct position using a footswitch, computer mouse, keyboard, or other input means. Alternatively, the computer may automatically determine when the fingertips are in the correct position merely by particular movements made by the fingertip device (e.g., if the pinkie is moved a particular direction) or based on an elapsed time period, etc. Accordingly, at each prompted step, the computer may record the measurements at step 2708 and perform any calculations necessary to transform the measurements (e.g., difference/distance between two fingers) into usable information.

Such an interpolation/calculation process may involve relating the information to known statistical information (e.g., comparing the distance between two fingers that are placed around a particular joint with known statistics for such a joint distance/circumference). Further, the information may be displayed on a computer screen graphically so that the user (e.g., doctor) can effectively utilize the information and make adjustments as necessary.

The process of movements, calculations, etc. may also be recorded in a history of events that may be indexed, sorted, organized, viewed, edited, etc. as desired by the user(s).

In addition, as described above, the measurements and data may be used in specific medical contexts. For example, the measurements may comprise reference points of a first limb that is serving as a reference to a fractured bone on a second limb of the person being examined. The data is based on the first limb measurements are displayed on a display device and the examiner then performs a fracture reduction of the fractured bone using the displayed data. Further, the displayed data may assist the user by indicating whether a successful reduction has been achieved based on the reference points of the first limb and the measurements obtained from the sensor during the fracture reduction. In another context, the measurements may comprise a path traced by the examiner during the medical exam. The data may further comprise the length of a skeletal segment or the range of motion of a joint of the person being examined.

REFERENCES

[1] An, K. N.; Jacobsen, M. C.; Berglund, L. J.; and Chao, E. Y.: Application of a magnetic tracking device to kinesiologic studies. *J Biomech*, 21(7): 613-20, 1988

[2] Andriacchi, T. P.: Dynamics of pathological motion: applied to the anterior cruciate deficient knee. *J Biomech*, 23 Suppl 1: 99-105, 1990.

[3] Andriacchi, T. P.: Practical and theoretical considerations in the application in the development of clinical gait analysis. *Biomed Mater Eng*, 8(3-4): 137-43, 1998.

[4] Andriacchi, T. P.; Alexander, E. J.; Toney, M. K.; Dyrby, C.; and Sum, J.: A point cluster method for in vivo motion analysis: applied to a study of knee kinematics. *J Biomech Eng*, 120(6): 743-9, 1998.

[5] Andriacchi, T. P.; Dyrby, C. O.; and Johnson, T. S.: The use of functional analysis in evaluating knee kinematics. *Clin Orthop*, (410): 44-53, 2003.

[6] Andriacchi, T. P.; Lang, P. L.; Alexander, E. J.; and Hurwitz, D. E.: Methods for evaluating the progression of osteoarthritis. *J Rehabil Res Dev*, 37(2): 163-70, 2000.

[7] Chao, E. Y.; An, K. N.; Askew, L. J.; and Morrey, B. F.: Electrogoniometer for the measurement of human elbow joint rotation. *J Biomech Eng*, 102(4): 301-10, 1980.

[8] Harryman, D. T., 2nd; Sidles, J. A.; Clark, J. M.; McQuade, K. J.; Gibb, T. D.; and Matsen, F. A., 3rd: Translation of the humeral head on the glenoid with passive glenohumeral motion. *J Bone Joint Surg Am*, 72(9): 1334-43, 1990.

[9] Harryman, D. T., 2nd; Sidles, J. A.; Harris, S. L.; and Matsen, F. A., 3rd: The role of the rotator interval capsule in passive motion and stability of the shoulder. *J Bone Joint Surg Am*, 74(1): 53-66, 1992.

[10] Harryman, D. T.; Sidles, J. A.; Harris, S. L.; Lippitt, S. B.; and Matsen, F. A., 3rd: The effect of articular conformity and the size of the humeral head component on laxity and motion after glenohumeral arthroplasty. A study in cadavera. *J Bone Joint Surg Am*, 77(4): 555-63, 1995.

[11] Hsu, H. C.; Luo, Z. P.; Rand, J. A.; and An, K. N.: Influence of patellar thickness on patellar tracking and patellofemoral contact characteristics after total knee arthroplasty. *J Arthroplasty*, 11(1): 69-80, 1996.

[12] Hulet, C.; Hurwitz, D. E.; Andriacchi, T. P.; Galante, J. O.; and Vielpeau, C.: [Functional gait adaptations in patients with painful hip]. *Rev Chir Orthop Reparatrice Appar Mot*, 86(6): 581-9, 2000.

[13] Hurwitz, D. E.; Andriacchi, T. P.; Bush-Joseph, C. A.; and Bach, B. R., Jr.: Functional adaptations in patients with ACL-deficient knees. *Exerc Sport Sci Rev*, 25: 1-20, 1997.

[14] Hurwitz, D. E.; Foucher, K. C.; Sumner, D. R.; Andriacchi, T. P.; Rosenberg, A. G.; and Galante, J. O.: Hip motion and moments during gait relate directly to proximal femoral bone mineral density in patients with hip osteoarthritis. *J Biomech*, 31(10): 919-25, 1998.

[15] Hurwitz, D. E.; Hulet, C. H.; Andriacchi, T. P.; Rosenberg, A. G.; and Galante, J. O.: Gait compensations in patients with osteoarthritis of the hip and their relationship to pain and passive hip motion. *J Orthop Res*, 15(4): 629-35, 1997.

[16] Hurwitz, D. E.; Sumner, D. R.; Andriacchi, T. P.; and Sugar, D. A.: Dynamic knee loads during gait predict proximal tibial bone distribution. *J Biomech*, 31(5): 423-30, 1998.

[17] Johnson, T. S.; Andriacchi, T. P.; and Erdman, A. G.: Sensitivity of finite helical axis parameters to temporally varying realistic motion utilizing an idealized knee model. *Proc Inst Mech Eng [H]*, 218(2): 89-100, 2004.

[18] Lai, K. A.; Kuo, K. N.; and Andriacchi, T. P.: Relationship between dynamic deformities and joint moments in children with cerebral palsy. *J Pediatr Orthop*, 8(6): 690-5, 1988.

[19] McQuade, K. J.; Sidles, J. A.; and Larson, R. V.: Reliability of the Genucom Knee Analysis System. A pilot study. *Clin Orthop*, (245): 216-9, 1989.

[20] Morrey, B. F.; Askew, L. J.; and Chao, E. Y.: A biomechanical study of normal functional elbow motion. *J Bone Joint Surg Am*, 63(6): 872-7, 1981.

[21] Newcomer, K.; Laskowski, E. R.; Yu, B.; Larson, D. R.; and An, K. N.: Repositioning error in low back pain. Comparing trunk repositioning error in subjects with chronic low back pain and control subjects. *Spine*, 25(2): 245-50, 2000.

[22] Pearl, M. L.; Harris, S. L.; Lippitt, S. B.; Sidles, J. A.; Harryman, D. T., 2nd; and Matsen, F. A., 3rd: A system for describing positions of the humerus relative to the thorax and its use in the presentation of several functionally important arm positions. *J Shoulder Elbow Surg*, 1: 113-118, 1992.

[23] Pearl, M. L.; Jackins, S.; Lippitt, S. B.; Sidles, J. A.; and Matsen, F. A., 3rd: Humeroscapular positions in a shoulder range-of-motion-examination. *J Shoulder Elbow Surg*, 1: 296-305, 1992.

[24] Pearl, M. L.; Sidles, J. A.; Lippitt, S. B.; Harryman, D. T., 2nd; and Matsen, F. A., 3rd: Codman's paradox: Sixty years later. *J Shoulder Elbow Surg*, 1: 219-225, 1992.

[25] Pearl, M. L., and Wong, K.: Shoulder Kinematics and Kinesiology. Edited by Norris, T., Rosemont, AAOS, 2001.

[26] Ramsey, M.; Neale, P. G.; Morrey, B. F.; O'Driscoll S, W.; and An, K. N.: Kinematics and functional characteristics of the Pritchard ERS unlinked total elbow arthroplasty. *J Shoulder Elbow Surg*, 12(4): 385-90, 2003.

[27] Uchiyama, S.; Cooney, W. P., 3rd; Linscheid, R. L.; Niebur, G.; and An, K. N.: Kinematics of the proximal interphalangeal joint of the finger after surface replacement. *J Hand Surg [Am]*, 25(2): 305-12, 2000.

[28] Uchiyama, S.; Cooney, W. P.; Niebur, G.; An, K. N.; and Linscheid, R. L.: Biomechanical analysis of the trapeziometacarpal joint after surface replacement arthroplasty. *J Hand Surg [Am]*, 24(3): 483-90, 1999.

[29] Veeger, H. E.; Yu, B.; An, K. N.; and Rozendal, R. H.: Parameters for modeling the upper extremity. *J Biomech*, 30(6): 647-52, 1997.

[30] Pearl, M. L., Wong, K.: Shoulder Kinematics and Kinesiology. OKU: Shoulder and Elbow, ed 2. Editor, Tom Norris; 37-48, 2002.

[31] Delp, S L, Stulberg, S D, Davies, B, Picard, F, Leitner, F. Computer assisted knee replacement. Clin Orthop. 1998; 354:49-56.

CONCLUSION

This concludes the description of the preferred embodiment of the invention. The following describes some alternative embodiments for accomplishing the present invention. For example, any type of computer, such as a mainframe, minicomputer, or personal computer, or computer configuration, such as a timesharing mainframe, local area network, or standalone personal computer, could be used with the present invention.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A computer implemented method for conducting a medical exam comprising:
   (a) mounting a sensor on a fingertip of a finger of a first person, wherein the sensor is communicatively coupled to a computer;
   (b) calibrating the sensor using a known target;
   (c) engaging the finger having the sensor to perform a medical examination directly on a second person;
   (d) obtaining measurements from the sensor on the fingertip during the medical examination, wherein the measurements:
      (i) relate to a position of the sensor with respect to an anatomical element of the second person; and
      (ii) comprise a distance between a sensor on a left hand and a sensor on a right hand of the first person; and
   (e) obtaining data based on the measurements.

2. The method of claim 1, wherein the sensor comprises an electromagnetic motion sensor.

3. The method of claim 1, further comprising correcting all data using a best-fit calibration function prior to calibrating the sensor.

4. The method of claim 1, wherein the calibrating comprises:
- inserting the sensor into a calibration device prior to mounting the sensor on the fingertip, wherein the calibration device comprises one or more known points;
- storing coordinates of the one or more known points based on the sensor to provide one or more locations in space;
- touching the one or more known points in the calibration device with the sensor mounted on the fingertip to obtain coordinates of the sensor;
- subtracting the coordinates of the one or more known points from the coordinates of the sensor to provide a vector pointing from the sensor to the known point at the fingertip; and
- determining a matrix based on the vector that will rotate the vector to account for a position of the fingertip.

5. The method of claim 4, further comprising:
- determining if an accuracy of the coordinates of the sensor are within a defined threshold; and
- repeating the touching and determining steps until the accuracy of the coordinates of the sensor are within the defined threshold.

6. The method of claim 1, wherein multiple sensors are used on two or more fingertips of the user.

7. The method of claim 1, wherein the measurements comprise a distance between two sensors on a single hand of the first person.

8. The method of claim 1, wherein the measurements comprise a distance between a midpoint of two sensors on the right hand to a midpoint of two sensors on the left hand.

9. The method of claim 1, wherein the measurement comprises a depth of an object on the second person.

10. The method of claim 1, wherein the data obtained comprises a plot of the measurements on a display device of the computer.

11. The method of claim 1, wherein:
- the measurements comprise reference points of a first limb that is serving as a reference to a fractured bone on a second limb of the second person; and
- the data is displayed on a display device of the computer system;
- the first person utilizes the fingertip having the sensor to perform a fracture reduction on the fractured bone of the second person; and
- data is displayed during the fracture reduction, wherein the data indicates whether a successful reduction has been achieved based on the reference points of the first limb and the measurements obtained from the sensor during the fracture reduction.

12. The method of claim 1, wherein the measurements comprise a path traced by the first person with the finger during the medical examination.

13. The method of claim 1, wherein the data comprises a range of motion of a joint of the second person.

14. The method of claim 1, wherein the measurements comprise a length of a skeletal segment.

15. The method of claim 1, wherein the measurements are obtained for an object that is not directly visible by a human eye.

16. The method of claim 1, further comprising mounting a placement object comprised of a nub that assists the first person in finding a particular spot on the finger, wherein such a placement object enhances a precision of point localization.

17. An apparatus for conducting a medical exam comprising:
- (a) a computer;
- (b) a sensor adapted to be mounted on a fingertip of a finger of a first person, wherein the sensor is communicatively coupled to the computer; and
- (c) a known target, wherein the sensor is calibrated using the known target;

wherein:
- (i) the finger having the sensor performs a medical examination directly on a second person;
- (ii) measurements are obtained from the sensor on the fingertip during the medical examination, wherein the measurements relate to a position of the sensor with respect to an anatomical element of the second person;
- (iii) the measurements comprise a distance between a sensor on a left hand and a sensor on a right hand of the first person; and
- (iv) data based on the measurements is obtained and provided to the computer.

* * * * *